United States Patent [19]

Thomas

[11] Patent Number: 5,880,130
[45] Date of Patent: Mar. 9, 1999

[54] 4,6-DIANILINO-PYRIMIDINE DERIVATIVES, THEIR PREPARATION AND THEIR USE AS TYROSINE KINASE INHIBITORS

[75] Inventor: Andrew Peter Thomas, Congleton, United Kingdom

[73] Assignee: Zeneca Limited, London, United Kingdom

[21] Appl. No.: 663,200

[22] PCT Filed: Dec. 5, 1994

[86] PCT No.: PCT/GB94/02659

§ 371 Date: Jun. 7, 1996

§ 102(e) Date: Jun. 7, 1996

[87] PCT Pub. No.: WO95/15952

PCT Pub. Date: Jun. 15, 1995

[30] Foreign Application Priority Data

Dec. 9, 1993 [GB] United Kingdom .................. 9325217

[51] Int. Cl.$^6$ ...................... C07D 239/48; A61K 31/505
[52] U.S. Cl. ..................... 514/256; 544/326; 544/327; 544/328; 544/329
[58] Field of Search ............................ 514/256; 544/326, 544/327, 328, 329

[56] References Cited

U.S. PATENT DOCUMENTS 5,707,995   1/1998   Munro et al. ........................... 514/256

FOREIGN PATENT DOCUMENTS

| 139 613 | 5/1985 | European Pat. Off. . |
| 248 349 | 12/1987 | European Pat. Off. . |
| 516 588 | 12/1992 | European Pat. Off. . |
| 520 772 | 12/1992 | European Pat. Off. . |
| 564 409 | 10/1993 | European Pat. Off. . |
| 566 226 | 10/1993 | European Pat. Off. . |
| 0 602 851 | 6/1994 | European Pat. Off. . |
| 0 635 498 | 1/1995 | European Pat. Off. . |
| 0 635 507 | 1/1995 | European Pat. Off. . |
| 0 640 599 | 3/1995 | European Pat. Off. . |
| 92 20642 | 11/1992 | WIPO . |
| WO 94/00513 | 1/1994 | WIPO . |
| 94 02470 | 2/1994 | WIPO . |
| WO 94/07867 | 4/1994 | WIPO . |

OTHER PUBLICATIONS

Wheeler et al, Chemical Abstracts vol. 113, entry 212003.
Fry et al.; A Specific Inhibitor of the Epiderman Growth Factor Receptor Tyrosine Kinase; Science; 19 Aug. 1994; pp. 1093–1095.
Buchdunger et al.; 4,5–Dianilinophthalimide: A protein–tyrosine kinase . . . transduction pathway and potent in vivo activity; Proc. Natl. Acad. Sci. USA, Mar. 1994; pp. 2334–2338.
Ward et al.; Epidermal Growth Factor Receptor Tyrosine Kinase; Biochemical Pharmacology; 1994; pp. 659–666.
Rewcastle et al.; Tyrosine Kinase Inhibitors. 5. Synthesis and Structure–Activity Relationships . . . Domain of the Epidermal Growth Factor Receptor; J. Med. Chem.; 1995; pp. 3482–3487.

Spence; Inhibitors of Tyrosine Kinase Activity as Anticancer Therapeutics: Recent Developments; Current Drugs Ltd., Anticancers etc., Patent Update; Therapeutic Patents, Jan. 1993; pp. 3–9.
Spada et al., Small molecule inhibitors of tyrosine kinase activity; Ex. Opin. Ther. Patents; 1995, pp. 805–817.
Bridges; The current status of tyrosine kinase inhibitors: . . . EGF receptor represent a new beginning?; Ex. Opin. Ther. Patents; 1995.
Traxler et al.; Recent advances in protein tyrosine kinase inhibitors; Drugs of the Future; 1995; pp. 1261–1274.
Abstract, WO 95/09847 (German), 13 Apr. 1995; Derwent Abstract 95/155198/20.
Abstract, WO 95/09851 (German), 13 Apr. 1995; Derwent Abstract 95/ 155200/20.
Abstract, WO 95/09852 (German), 13 Apr. 1995; Derwent Abstract 95/ 155201/20.
Abstract, WO 95/ 09853 (German), 13 Apr. 1995; Derwent Abstract 95/ 155202/20.
Burke: "Protein–tyrosine kinase inhibitors", Drugs Of The Future, vol. 17, No. 2, 1992, pp. 119–131, see the whole document.
Trinks, et al: "Dianilinophthalimides: Potent and selective, ATP–competitive inhibitors of the EGF–receptor protein tyrosine kinase", Journal Of Medicinal Chemistry, vol. 37, No. 7, Apr. 1, 1994, pp. 1015–1027, see the whole document.
Derwent Abstract No. 85–099057/ 17 of AU 84/32450 (equivalent to and EPA 139613 cited in Jun. 7, 1996 PTO–1449.
Derwent Abstract 87–343301/49 (EP–248349 cited in Jun. 7, 1996 PTO–1449).
Derwent Abstract 92–400924/49 (EP 516588 cited in Jun. 7, 1996 PTO–1449).
Derwent Abstract 93–313740/40 (EP 564409 cited in Jun. 7, 1996 PTO–1449).

Primary Examiner—John M. Ford
Attorney, Agent, or Firm—Cushman Darby & Cushman Intellectual Property Group of Pillsbury Madison & Sutro, LLP

[57] ABSTRACT

The invention concerns pyrimidine derivatives of formula wherein m is 1, 2 or 3; each $R^1$ is independently hydrogen, hydroxy, (un)substituted amino, nitro, halogeno, cyano, carboxy, (un)substituted carbamoyl, ureido, (1–4C)alkoxycarbonyl, (un)substituted (1–4C)alkyl, (un)substituted (1–4C)alkoxy, (1–3C)alkylenedioxy, (1–4C)alkylthio, (1–4C)alkylsulphinyl, (1–4C)alkyl-sulphonyl, (2–4C)alkanoyloxy; n is 1, 2 or 3; and each $R^2$ is independently hydrogen, hydroxy, halogeno, trifluoromethyl, trifluoromethoxy, amino, nitro, cyano, (1–4C)alkyl, (1–4C)alkoxy, (1–4C)alkylamino, di-[(1–4C)alkyl]amino, (1–4C)alkylthio, (1–4C)alkylsulphinyl, (1–4C)alkylsulphonyl, (2–4C)alkanoylamino, (2–4C)alkanoyl or (1–3C)alkylenedioxy; or a pharmaceutically-acceptable salt thereof; processes for their preparation; pharmaceutical compositions containing them; and the use of the receptor tyrosine kinase inhibitory properties of the compounds in the treatment of cell-proliferation diseases.

22 Claims, No Drawings

4,6-DIANILINO-PYRIMIDINE DERIVATIVES, THEIR PREPARATION AND THEIR USE AS TYROSINE KINASE INHIBITORS

This application claims benefit of international application PCT/GB94/02659 filed Dec. 5, 1994.

The invention relates to pyrimidine derivatives, or pharmaceutically-acceptable salts thereof, which possess anti-cell-proliferation activity such as anti-cancer activity and are accordingly useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

Many of the current treatment regimes for cancer utilise compounds which inhibit DNA synthesis. Such compounds are toxic to cells generally but their toxic effect on the rapidly dividing tumour cells can be beneficial. Alternative approaches to anti-cancer agents which act by mechanisms other than the inhibition of DNA synthesis have the potential to display enhanced selectivity of action against cancer cells.

In recent years it has been discovered that a cell may become cancerous by virtue of the transformation of a portion of its DNA into an oncogene i.e. a gene which, on activation, leads to the a formation of malignant tumour cells (Bradshaw, *Mutagenesis*, 1986, 1, 91). Several such oncogenes give rise to the production of peptides which are receptors for growth factors. The growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al. *Ann. Reports in Med. Chem.* 1989, Chpt. 13).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43–73) based on families of growth factors which bind to different receptor tyrosine kinases. The classification includes Class I receptor tyrosine kinases comprising the EGF family of receptor tyrosine kinases such as the EGF, NEU, erbB, Xmrk, DER and let23 receptors, Class II receptor tyrosine kinases comprising the insulin family of receptor tyrosine kinases such as the insulin, IGFI and insulin-related receptor (IRR) receptors and Class III receptor tyrosine kinases comprising the platelet-derived growth factor (PDGF) family of receptor tyrosine kinases such as the PDGFA, PDGFP and colony-stimulating factor 1 (CSF1) receptors. It is known that Class I kinases such as the EGF family of receptor tyrosine kinases are frequently present in common human cancers such as breast cancer (Sainsbury et al., *Brit. J. Cancer*, 1988, 58, 458; Guerin et al., *Oncogene Res.*, 1988, 3, 21), squamous cell cancer of the lung (Hendler et al., *Cancer Cells*, 1989, 7, 347), bladder cancer (Neal et al., *Lancet*, 1985, 366), oesophageal cancer (Mukaida et al, *Cancer*, 1991, 68, 142), gastrointestinal cancer such as colon, rectal or stomach cancer (Bolen et al., *Oncogene Res.*, 1987, 1, 149), leukaemia (Konaka et al., *Cell*, 1984, 37, 1035) and ovarian, bronchial or pancreatic cancer (European Patent Specification No. 0400586). As further human tumour tissues are tested for the EGF family of receptor tyrosine kinases it is expected that its widespread prevalance will be established in further cancers such as thyroid and uterine cancer. It is also known that EGF type tyrosine kinase activity is rarely detected in normal cells whereas it is more frequently detectable in malignant cells (Hunter, *Cell*, 1987, 50, 823). It has been shown more recently (W J Gullick, *Brit. Med. Bull.*, 1991, 47, 87) that EGF receptors which possesses tyrosine kinase activity are overexpressed in many human cancers such as brain, lung squamous cell, bladder, gastric, breast, head and neck, oesophageal, gynaecological and thyroid tumours. It is also expected that receptor tyrosine kinases will prove to be important in other cell-proliferation diseases such as psoriasis.

Accordingly it has been recognised that an inhibitor of receptor tyrosine kinases should be of value as a selective inhibitor of the growth of mammalian cancer cells (Yaish et al. *Science*, 1988, 242, 933). Support for this view is provided by the demonstration that erbstatin, an EGF receptor tyrosine kinase inhibitor, specifically attenuates the growth in athymic nude mice of a transplanted human mammary carcinoma which expresses EGF receptor tyrosine kinase but is without effect on the growth of another carcinoma which does not express EGF receptor tyrosine kinase (Toi et al., *Eur. J. Cancer Clin. Oncol.*, 1990, 26, 722.) Various derivatives of styrene are also stated to possess tyrosine kinase inhibitory properties (European Patent Application Nos. 0211363, 0304493 and 0322738) and to be of use as anti-tumour agents. The in vivo inhibitory effect of two such styrene derivatives which are EGF receptor tyrosine kinase inhibitors has been demonstrated against the growth of human squamouis cell carcinoma inoculated into nude mice (Yoneda et al., *Cancer Research*, 1991, 51, 4430). Accordingly it has been indicated that Class I receptor tyrosine kinase inhibitors will prove to be useful in the treatment of a variety of human cancers. Various known tyrosine kinase inhibitors are disclosed in a more recent review by T R Burke Jr. (*Drugs of the Future*, 1992, 17, 119).

It is further known from European Patent Application No. 0564409 that certain 2-anilinopyrimidine derivatives are selective inhibitors of protein kinases such as protein kinase C and are at least 100-fold less potent as inhibitors of other kinases such as PDGF receptor tyrosine kinase. The compounds are stated to be useful in the treatment of atherosclerosis, thrombosis and in the treatment of tumours.

It is also known from the patent application WO 92/20642 that certain aryl and heteroaryl compounds inhibit EGF and/or PDGF receptor tyrosine kinase. There is the disclosure of certain pyrimidine derivatives but there is no specific disclosure of 4,6-dianilinopyrimidine derivatives.

It is also known from European Patent Applications Nos. 0520722 and 0566226 that certain 4-anilinoquinazoline derivatives are useful as inhibitors of receptor tyrosine kinase.

It is also known from patent application WO 94/02470 that certain substituted pyrimidine compounds, including 4,6-di-(3'-trifluoromethylanilino)pyrimidine, are useful as pesticides.

We have now found that certain 4,6-dianilinopyrimidine derivatives possess anti-cell-proliferation properties which are believed to arise from their Class I receptor tyrosine kinase inhibitory activity.

According to the invention there is provided a pyrimidine derivative of the formula I

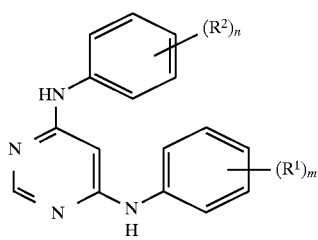

wherein m is 1, 2 or 3;

each R¹ is independently hydrogen, hydroxy, amino, nitro, halogeno, cyano, carboxy, carbamoyl, ureido, N-(1–4C)alkylcarbamoyl, N,N-di-[(1–4C)alkyl]carbamoyl, (1–4C)alkoxycarbonyl, (1–4C)alkyl, (1–4C)alkoxy, (1–3C)alkylenedioxy, (1–4C)alkylamino, di-[(1–4C)alkyl]amino, (1–4C)alkylthio, (1–4C)alkylsulphinyl, (1–4C)alkylsulphonyl, hydroxy-(1–4C)alkyl, (1–4C)alkoxy-(1–4C)alkyl, halogeno-(1–4C)alkyl, (2–4C)alkanoyloxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]carbamoyl-(1–4C)alkyl, amino-(1–4C)alkyl, (1–4C)alkylamino-(1–4C)alkyl, di-[(1–4C)alkyl]amino-(1–4C)alkyl, cyano-(1–4C)alkyl, hydroxy-(2–4C)alkoxy, (1–4C)alkoxy-(2–4C)alkoxy, halogene-(1–4C)alkoxy, (2–4C)alkanoyloxy-(2–4C)alkoxy, carboxy-(1–4C)alkoxy, (1–4C)alkoxycarbonyl-(1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, N-[hydroxy-(2–4C)alkyl]carbamoyl-(1–4C)alkoxy, N,N-di-[hydroxy-(2–4C)alkyl]carbamoyl-(1–4C)alkoxy, amino-(2–4C)alkoxy, (1–4C)alkylamino-(2–4C)alkoxy, di-[(1–4C)alkyl]amino-(2–4C)alkoxy, N-[hydroxy-(2–4C) alkyl]amino-(2–4C)alkoxy, N,N-di-[hydroxy-(2–4C)alkyl]amino-(2–4C)alkoxy, N-[hydroxy-(2–4C)alkyl]-N-[(1–4C)alkyl]amino-(2–4C)alkoxy, amino-(2–4C)alkoxy-(2–4C)alkoxy, N-[(1–4C)alkyl]amino-(2–4C)alkoxy-(2–4C)alkoxy, N,N-di-[(1–4C)alkyl]amino-(2–4C)alkoxy-(2–4C)alkoxy, N-[hydroxy-(2–4C)alkyl]amino-(2–4C)alkoxy-(2–4C)alkoxy, N,N-di-[hydroxy-(2–4C)alkyl]amino-(2–4C)alkoxy-(2–4C)alkoxy, N-[hydroxy-(2–4C)alkyl]-N-[(1–4C)alkyl]amino-(2–4C)alkoxy-(2–4C)alkoxy, amino-hydroxy-(2–4C)alkoxy, N-[(1–4C)alkyl]amino-hydroxy-(2–4C)alkoxy, N,N-di-[(1–4C)alkyl]amino-hydroxy-(2–4C)alkoxy, N-[hydroxy-(2–4C)alkyl]amino-hydroxy-(2–4C)alkoxy, N,N-di-[hydroxy-(2–4C)alkyl]amino-hydroxy-(2–4C)alkoxy, N-[hydroxy-(2–4C)alkyl]-N-[(1–4C)alkyl]amino-hydroxy-(2–4C)alkoxy, amino-hydroxy-(2–4C)alkoxy-(2–4C)alkoxy, N-[(1–4C)alkyl]amino-hydroxy-(2–4C)alkoxy-(2–4C)alkoxy, N,N-di-[(1–4C)alkyl]amino-hydroxy-(2–4C)alkoxy-(2–4C)alkoxy, N-[hydroxy-(2–4C)alkyl]amino-hydroxy-(2–4C)alkoxy-(2–4C)alkoxy, N,N-di-[hydroxy-(2–4C)alkyl]amino-hydroxy-(2–4C)alkoxy-(2–4C)alkoxy, di-hydroxy-(2–4C)alkoxy, (1–4C)alkoxy-hydroxy-(2–4C)alkoxy, hydroxy-(2–4C)alkoxy-hydroxy-(2–4C)alkoxy, di-hydroxy-(2–4C)alkoxy-(2–4C)alkoxy, (1–4C)alkoxy-hydroxy-(2–4C)alkoxy-(2–4C)alkoxy, hydroxy-(2–4C)alkoxy-hydroxy-(2–4C)alkoxy-(2–4C)alkoxy, N-[amino-(2–4C)alkyl]carbamoyl-(1–4C)alkoxy, N-[N-{(1–4C)alkyl}amino-(2–4C)alkyl]carbamoyl-(1–4C)alkoxy, N-[N,N-di-{(1–4C)alkyl}amino-(2–4C)alkyl]carbamoyl-(1–4C)alkoxy, N-[N-{hydroxy-(2–4C)alkyl}amino-(2–4C)alkyl]carbamoyl-(1–4C)alkoxy, N-[N-{hydroxy-(2–4C)alkyl}-N-{(1–4C)alkyl}amino-(2–4C)alkyl]carbamoyl-(1–4C)alkoxy, N-[di-{hydroxy-(2–4C)alkyl}amino-(2–4C)alkyl]carbamoyl-(1–4C)alkoxy, N-[amino-(2–4C)alkyl]carbamoyl-(1–4C)alkoxy-(2–4C)alkoxy, N-[N-{(1–4C)alkyl}amino-(2–4C)alkyl]carbamoyl-(1–4C)alkoxy-(2–4C)alkoxy, N-[N,N-di-{(1–4C)alkyl}amino-(2–4C)alkyl]carbamoyl-(1–4C)alkoxy-(2–4C)-alkoxy, N-[N-{hydroxy-(2–4C)alkyl}amino-(2–4C)alkyl]carbamoyl-(1–4C)alkoxy-(2–4C)-alkoxy, N-[N-{hydroxy-(2–4C)alkyl}-N-{(1–4C)alkyl}amino-(2–4C)alkyl]carbamoyl-(1–4C)alkoxy-(2–4C)alkoxy, N-[N,N-di-{hydroxy-(2–4C)alkyl}amino-(2–4C)alkyl]carbamoyl-(1–4C)alkoxy-(2–4C)alkoxy, (2–4C)alkanoyloxy, (2–4C)alkanoylamino, N-[hydroxy-(2–4C)alkyl]amino, N-[hydroxy-(2–4C)alkyl]-N-[(1–4C)alkyl]amino or (1–4C)alkylsulphonylamino;

n is 1, 2 or 3; and each R² is independently hydrogen, hydroxy, halogeno, trifluoromethyl, trifluoromethoxy, amino, nitro, cyano, (1–4C)alkyl, (1–4C)alkoxy, (1–4C)alkylamino, di-[(1–4C)alkyl]amino, (1–4C)alkylthio, (1–4C)alkylsulphinyl, (1–4C)alkylsulphonyl, (2–4C)alkanoylamino, (2–4C)alkanoyl or (1–3C)alkylenedioxy; or a pharmaceutically-acceptable salt thereof; except that 4,6-di-(3'-trifluoromethylanilino)pyrimidine is excluded.

In this-specification the term "alkyl" includes both straight and branched chain alkyl groups but references to individual alkyl groups such as "propyl" are specific for the straight chain version only. An analogous convention applies to other generic terms.

According to a further aspect of the invention there is provided a pyrimidine derivative of the formula I wherein m is 1, 2 or 3;

each R¹ is independently hydrogen, hydroxy, amino, nitro, halogeno, cyano, carboxy, carbamoyl, ureido, N-(1–4C)alkylcarbamoyl, N,N-di-[(1–4C)alkyl]carbamoyl, (1–4C)alkoxycarbonyl, (1–4C)alkyl, (1–4C)alkoxy, (1–3C)alkylenedioxy, (1–4C)alkylamino, di-[(1–4C)alkyl]amino, (1–4C)alkylthio, (1–4C)alkylsulphinyl, (1–4C)alkylsulphonyl, hydroxy-(1–4C)alkyl, (1–4C)alkoxy-(1–4C)alkyl, halogeno-(1–4C)alkyl,-(2–4C)alkanoyloxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]carbamoyl-(1–4C)alkyl, amino-(1–4C)alkyl, (1–4C)alkylamino-(1–4C)alkyl, di-[(1–4C)alkyl]amino-(1–4C)alkyl, cyano-(1–4C)alkyl, hydroxy-(2–4C)alkoxy, (1–4C)alkoxy-(2–4C)alkoxy, halogeno-(1–4C)alkoxy, (2–4C)alkanoyloxy-(2–4C)alkoxy, carboxy-(1–4C)alkoxy, (1–4C)alkoxycarbonyl-(1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, amino-(2–4C)alkoxy, (1–4C)alkylamino-(2–4C)alkoxy, di-[(1–4C)alkyl]amino-(2–4C)alkoxy, (2–4C)alkanoyloxy, (2–4C)alkanoylamino or (1–4C)alkylsulphonylamino;

n is 1, 2 or 3; and each R² is independently hydrogen, hydroxy, halogeno, trifluoromethyl, trifluoromethoxy, amino, nitro, cyano, (1–4C)alkyl, (1–4C)alkoxy, (1–4C)alkylamino, di-[

(1–4C)alkyl]amino, (1–4C)alkylthio, (1–4C) alkylsulphinyl, (1–4C)alkylsulphonyl, (2–4C) alkanoylamino, (2–4C)alkanoyl or (1–3C) alkylenedioxy; or a pharmaceutically-acceptable salt thereof; except that 4,6-di-(3'-trifluoromethylanilino) pyrimidine is excluded.

The pyrimidine derivatives of the formula I are unsubstituted at the 2- and 5-positions.

It is also to be understood that certain pyrimidine derivatives of the formula I can exist in solvated as well as unsolvated forms such as, for example, hydrated forms. It is to be understood that the invention encompasses all such solvated forms which possess anti-cancer activity.

Suitable values for the generic radicals referred to above include those set out below.

A suitable value for $R^1$ or $R^2$ when it is halogeno is, for example, fluoro, chloro, bromo and iodo; when it is (1–4C) alkyl is, for example, methyl, ethyl, propyl, isopropyl, butyl, isobutyl, sec-butyl or tert-butyl; when it is (1–4C)alkoxy is, for example, methoxy, ethoxy, propoxy, isopropoxy or butoxy; when it is (1–4C)alkylamino is, for example, methylamino, ethylamino or propylamino; when it is di-[(1–4C)alkyl]amino is, for example, dimethylamino, N-ethyl-N-methylamino, diethylamino, N-methyl-N-propylamino or dipropylamino; when it is (1–4C)alkylthio is, for example, methylthio, ethylthio or propylthio; when it is (1–4C)alkylsulphinyl is, for example, methylsulphinyl, ethylsulphinyl or propylsulphinyl; when it is (1–4C) alkylsulphonyl is, for example, methylsulphonyl, ethylsulphonyl or propylsulphonyl; when it is (2–4C)alkanoylamino is, for example, acetamido, propionamido or butyramido; and when it is (1–3C)alkylenedioxy is, for example, methylenedioxy, ethylenedioxy or propylenedioxy.

Suitable values for each $R^1$ substituent which may be present include, for example:

for (1–4C)alkoxycarbonyl:
methoxycarbonyl, ethoxycarbonyl, propoxycarbonyl and tert-butoxycarbonyl;

for N-(1–4C)alkylcarbamoyl:
N-methylcarbamoyl, N-ethylcarbamoyl and N-propylcarbamoyl;

for N,N-di-[(1–4C)alkyl]carbamoyl:
N,N-dimethylcarbamoyl, N-ethyl-N-methylcarbamoyl and N,N-diethylcarbamoyl;

for halogeno-(1–4C)alkyl:
fluoromethyl, chloromethyl, bromomethyl, difluoromethyl, dichloromethyl, dibromomethyl, trifluoromethyl, 2-fluoroethyl, 2-chloroethyl and 2-bromoethyl;

for hydroxy-(1–4C)alkyl:
hydroxymethyl, 1-hydroxyethyl, 2-hydroxyethyl and 3-hydroxypropyl;

for (2–4C)alkanoyloxy-(1–4C)alkyl:
acetoxymethyl, propionyloxymethyl, butyryloxymethyl, 2-acetoxyethyl and 3-acetoxypropyl;

for (1–4C)alkoxy-(1–4C)alkyl:
methoxymethyl, ethoxymethyl, 1-methoxyethyl, 2-methoxyethyl, 2-ethoxyethyl and 3-methoxypropyl;

for carboxy-(1–4C)alkyl:
carboxymethyl, 1-carboxyethyl, 2-carboxyethyl and 3-carboxypropyl;

for (1–4C)alkoxycarbonyl-(1–4C)alkyl:
methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;

for carbamoyl-(1–4C)alkyl:
carbamoylmethyl, 1-carbamoylethyl, 2-carbamoylethyl and 3-carbamoylpropyl;

for N-(1–4C)alkylcarbamoyl-(1–4C)alkyl:
N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;

for N,N-di-[(1–4C)alkyl]carbamoyl-(1–4C)alkyl:
N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl;

for amino-(1–4C)alkyl:
aminomethyl, 1-aminoethyl, 2-aminoethyl and 3-aminopropyl;

for (1–4C)alkylamino-(1–4C)alkyl:
methylaminomethyl, ethylaminomethyl, 1-methylaminoethyl, 2-methylaminoethyl, 2-ethylamimoethyl and 3-methylaminopropyl;

for di-[(1–4C)alkyl]amino-(1–4C)alkyl:
dimethylaminomethyl, diethylaminomethyl, 1-dimethylaminoethyl, 2-dimethylaminoethyl and 3-dimethylaminopropyl;

for cyano-(1–4C)alkyl:
cyanomethyl, 2-cyanoethyl and 3-cyanopropyl;

for halogeno-(1–4C)alkoxy:
difluoromethoxy, trifluoromethoxy, 2-fluoroethoxy, 2-chloroethoxy, 2-bromoethoxy, 3-fluoropropoxy and 3-chloropropoxy;

for hydroxy-(2–4C)alkoxy:
2-hydroxyethoxy, 3-hydroxypropoxy and 4-hydroxybutoxy;

for (2–4C)alkanoyloxy-(2–4C)alkoxy:
2-acetoxyethoxy, 2propionyloxyethoxy, 2-butyryloxyethoxy and 3-acetoxypropoxy;

for (1–4C)alkoxy-(2–4C)alkoxy:
2-methoxyethoxy, 2-ethoxyethoxy, 3-methoxypropoxy and 4-methoxybutoxy;

for carboxy-(1–4C)alkoxy:
carboxymethoxy, 1-carboxyethoxy, 2-carboxyethoxy and 3-carboxypropoxy;

for (1–4C)alkoxycarbonyl-(1–4C)alkoxy:
methoxycarbonylmethoxy, ethoxycarbonylmethoxy, 1-methoxycarbonylethoxy, 2-methoxycarbonylethoxy, 2-ethoxycarbonylethoxy and 3-methoxycarbonylpropoxy;

for cyano-(1–4C)alkoxy:
cyanomethoxy, 1-cyanoethoxy, 2-cyanoethoxy and 3-cyanopropoxy;

for carbamoyl-(1–4C)alkoxy:
carbamoylmethoxy, 1-carbamoylethoxy, 2-carbamoylethoxy and 3-carbamoylpropoxy;

for N-(1–4C)alkylcarbamoyl-(1–4C)alkoxy:
N-methylcarbamoylmethoxy, N-ethylcarbamoylmethoxy, 2-(N-methylcarbamoyl)ethoxy, 2-(N-ethylcarbamoyl)ethoxy and 3-(N-methylcarbamoyl)propoxy;

for N,N-di-[(1–4C)alkyl]carbamoyl-(1–4C)alkoxy:
N,N-dimethylcarbamoylmethoxy, N-ethyl-N-methylcarbamoylmethoxy, N,N-diethylcarbamoylmethoxy, 2-(N,N-dimethylcarbamoyl)ethoxy, 2-(N,N-diethylcarbamoyl)ethoxy and 3-(N,N-dimethylcarbamoyl)propoxy;

for N-[hydroxy-(2–4C)alkyl]carbamoyl-(1–4C)alkoxy:
N-(2-hydroxyethyl)carbamoylmethoxy, 2-[N-(2-hydroxyethyl)carbamoyl]ethoxy and 3-[N-(3-hydroxypropyl)carbamoyl]propoxy;

for N,N-di-[hydroxy-(2–4C)alkyl]carbamoyl-(1–4C)alkoxy:
N,N-di-[2-hydroxyethyl]carbamoylmethoxy, and 2-[N,N-di-(2-hydroxyethyl)carbamoyl]ethoxy;

for amino-(2–4C)alkoxy:
2-aminoethoxy and 3-aminopropoxy;

for (1–4C)alkylamino-(2–4C)alkoxy:
2-(methylamino)ethoxy, 2-(ethylamino)ethoxy, 2-(propylamino)ethoxy, 3-(methylamino)propoxy and 3-(ethylamino)propoxy;

for di-[(1–4C)alkyl]amino-(2–4C)alkoxy:
2-(dimethylamino)ethoxy, 2-(N-ethyl-N-methylamino)ethoxy, 2-(diethylamino)ethoxy, 2-(dipropylamino)ethoxy, 3-(dimethylamino)propoxy and 3-(diethylamino)propoxy;

for N-[hydroxy-(2–4C)alkyl]amino-(2–4C)alkoxy:
2-(2-hydroxyethylamino)ethoxy, 3-(2-hydroxyethylamino)propoxy and 2-(3-hydroxypropylamino)ethoxy;

for N,N-di-[hydroxy-(2–4C)alkyl]amino-(2–4C)alkoxy:
2-[N,N-di-(2-hydroxyethyl)amino]ethoxy, 3-[N,N-di-(2-hydroxyethyl)amino]propoxy and 2-[N,N-di-(3-hydroxypropyl)amino]ethoxy;

for N-[hydroxy-(2–4C)alkyl]N-[(1–4C)alkyl]amino-(2–4C)alkoxy:
2-[N-(2-hydroxyethyl)-N-methylamino]ethoxy, 2-[N-(2-hydroxyethyl)-N-ethylamino]ethoxy and 3-[N-(3-hydroxypropyl)-N-ethylamino]propoxy;

for amino-(2–4C)alkoxy-(2–4C)alkoxy:
2-[2-aminoethoxy]ethoxy and 2-[3-aminopropoxy]ethoxy;

for N-[(1–4C)alkyl]amino-(2–4C)alkoxy-(2–4C)alkoxy:
2-(2-methylaminoethoxy)ethoxy, 2-(3-methylaminopropoxy)ethoxy and 2-(2-ethylaminoethoxy)ethoxy;

for N,N-di-[(1–4C)alkyl]amino-(2–4C)alkoxy-(2–4C)alkoxy: 2-(2-dimethylaminoethoxy)ethoxy, 2-(3-dimethylaminopropoxy)ethoxy and 2-(2-diethylaminoethoxy)ethoxy;

for N-[hydroxy-(2–4C)alkyl]amino-(2–4C)alkoxy-(2–4C)alkoxy:
2-[2-(2-hydroxyethylamino)ethoxy]ethoxy, 2-[3-(2-hydroxyethylamino)-propoxy]ethoxy and 3-[2-(3-hydroxypropylamino) ethoxy]propoxy;

for N,N-di-[hydroxy-(2–4C)alkyl]amino-(2–4C)alkoxy-(2–4C)alkoxy:
2-[2-di-(2-hydroxyethyl)aminoethoxy]ethoxy, 3-[2-di-(2-hydroxyethyl)aminoethoxy]propoxy, 2-[2-di-(3-hydroxypropyl)aminoethoxy]ethoxy and 2-[3-di-(2-hydroxyethyl)aminopropoxy]ethoxy;

for N-[hydroxy-(2–4C)alkyl]N-[(1–4C)alkyl]amino-(2–4C)alkoxy-(2–4C)alkoxy:
2-[2-{N-(2-hydroxyethyl)-N-methylamino}ethoxy]ethoxy, 2-[2-{N-(3-hydroxypropyl)-N-methylamino}ethoxy]ethoxy and 2-[3-{N-(2-hydroxyethyl)-N-ethylamino}propoxy]ethoxy;

for amino-hydroxy-(2–4C)alkoxy:
2-amino-2-hydroxyethoxy, 3-amino-2-hydroxypropoxy and 3-amino-3-hydroxypropoxy;

for N-[(1–4C)alkyl]amino-hydroxy-(2–4C)alkoxy:
3-methylamino-2-hydroxypropoxy and 4-methylamino-3-hydroxybutoxy;

for N,N-di-[(1–4C)alkyl]amino-hydroxy-(2–4C)alkoxy:
3-dimethylamino-2-hydroxypropoxy and 4-dimethylamino-3-hydroxybutoxy;

for N-[hydroxy-(2–4C)alkyl]amino-hydroxy-(2–4C)alkoxy:
3-(2-hydroxyethyl)amino-2-hydroxypropoxy and 4-(2-hydroxyethyl)amino-3-hydroxybutdxy;

for N,N-di-[hydroxy-(2–4C)alkyl]amino-hydroxy-(2–4C)alkoxy:
3-[di-(2-hydroxyethyl)amino]2-hydroxypropoxy and 4-[di-(2-hydroxyethyl)amino]3-hydroxybutoxy;

for N-[hydroxy-(2–4C)alkyl]N-[(1–4C)alkyl]amino-hydroxy-(2–4C)alkoxy:
3-[N-(2-hydroxyethyl)-N-methylamino]2-hydroxypropoxy and 4-[N-(2-hydroxyethyl)-N-methylamino]3-hydroxybutoxy;

for amino-hydroxy-(2–4C)alkoxy-(2–4C)alkoxy:
3-amino-2-(2-hydroxyethoxy)propoxy and 4-amino-3-(2-hydroxyethoxy)butoxy;

for N-[(1–4C)alkyl]amino-hydroxy-(2–4C)alkoxy-(2–4C)alkoxy:
3-methylamino-2-(2-hydroxyethoxy)propoxy, 3-ethylamino-2-(2-hydroxyethoxy)propoxy and 4-methylamino-3-(2-hydroxyethoxy)butoxy;

for N,N-di-[(1–4C)alkyl]amino-hydroxy-(2–4C)alkoxy-(2–4C)alkoxy:
3-diethylamino-2-(2-hydroxyethoxy)propoxy and 4-dimethylamino-3-(2-hydroxyethoxy)butoxy;

for N-[hydroxy-(2–4C)alkyl]amino-hydroxy-(2–4C)alkoxy-(2–4C)alkoxy:
3-(2-hydroxyethyl)amino-2-(2-hydroxyethoxy)propoxy and 4-(2-hydroxyethyl)amino-3-(2-hydroxyethoxy)butoxy;

for N,N-di-[hydroxy-(2–4C)alkyl]amino-hydroxy-(2–4C)alkoxy-(2–4C)alkoxy:
3-[di-(2-hydroxyethyl)amino]2-(2-hydroxyethoxy)propoxy and 4-[di-(2-hydroxyethyl)amino]3-(2-hydroxyethoxy)butoxy;

for di-hydroxy-(2–4C)alkoxy:
2,3-dihydroxypropoxy and 3,4-dihydroxybutoxy;

for (1–4C)alkoxy-hydroxy-(2–4C)alkoxy:
3-methoxy-2-hydroxypropoxy and 4-methoxy-3-hydroxybutoxy;

for hydroxy-(2–4C)alkoxy-hydroxy-(2–4C)alkoxy:
3-(2-hydroxyethoxy)-2-hydroxypropoxy and 4-(2-hydroxyethoxy)-3-hydroxybutoxy;

for di-hydroxy-(2–4C)alkoxy-(2–4C)alkoxy:
3-(2,3-dihydroxypropoxy)propoxy and 4-(2,3-dihydroxypropoxy)butoxy;

for (1–4C)alkoxy-hydroxy-(2–4C)alkoxy-(2–4C)alkoxy:
3-methoxy-2-(2-hydroxyethoxy)propoxy and 4-methoxy-3-(2-hydroxy-ethoxy)butoxy;

for hydroxy-(2–4C)alkoxy-hydroxy-(2–4C)alkoxy-(2–4C)alkoxy:
3-(2-hydroxyethoxy)-2-(2-hydroxyethoxy)propoxy and 4-(2-hydroxyethoxy)-3-(2-hydroxyethoxy)butoxy;

for N-[amino-(2–4C)alkyl]carbamoyl-(1–4C)alkoxy:
N-(aminoethyl)carbamoylmethoxy and 2-[N-(2-aminoethyl)carbamoyl]ethoxy;

for N-[N-{(1–4C)alkyl}amino-(2–4C)alkyl]carbamoyl-(1–4C)alkoxy:
N-(2-methylaminoethyl)carbamoylmethoxy and 2-[N-(2-methylaminoethyl)carbamoyl]ethoxy;

for N-[N,N-di-{(1–4C)alkyl}amino-(2–4C)alkyl]carbamoyl-(1–4C)alkoxy:
N-(2-dimethylaminoethyl)carbamoylmethoxy, 2-[N-(2-dimethylamino-ethyl)carbamoyl]ethoxy;

for N-[N-{hydroxy-(2–4C)alkyl}amino-(2–4C)alkyl]carbamoyl-(1–4C)alkoxy:
N-[2-(2-hydroxyethyl)aminoethyl]carbamoylmethoxy, 2-[N-{2-(2-hydroxyethyl)aminoethyl}carbamoyl]ethoxy;

for N-[N-{hydroxy-(2–4C)alkyl}-N-{(1–4C)alkyl}amino-(2–4C)alkyl]carbamoyl-(1–4C)alkoxy:
N-[2-{N-(2-hydroxyethyl)-N-methylamino}ethyl]carbamoylmethoxy and 2-(N-[2-{N-(2-hydroxyethyl)-N-methylamino}ethyl]carbamoyl)ethoxy;

for N-[di-{hydroxy-(2–4C)alkyl}amino-(2–4C)alkyl]carbamoyl-(1–4C)alkoxy:
N-[2-{di-(2-hydroxyethyl)amino}-ethyl]carbamoylmethoxy and 2-[N-{2-di-(2-hydroxyethyl)aminoethyl]carbamoyl}ethoxy;

for N-[amino-(2–4C)alkyl]carbamoyl-(1–4C)alkoxy-(2–4C)alkoxy:
2-[N-(2-aminoethyl)carbamoylmethoxy]ethoxy and 2-[N-(3-aminopropyl)carbamoylmethoxy]ethoxy;

for N-[N-{(1–4C)alkyl}amino-(2–4C)alkyl]carbamoyl-(1–4C)alkoxy-(2–4C)alkoxy;
2-[N-(2-methylaminoethyl)carbamoylmethoxy]ethoxy and 3-[N-(2-methylaminoethyl)carbamoylmethoxy]propoxy;

for N-[N,N-di-{(1–4C)alkyl}amino-(2–4C)alkyl]carbamoyl-(1–4C)alkoxy-(2–4C)alkoxy:
2-[N-(2-dimethylaminoethyl)carbamoylmethoxy]ethoxy and 3-[N-(2-dimethylaminoethyl)carbamoylmethoxy]propoxy;

for N-[N-{hydroxy-(2–4C)alkyl}amino-(2–4C) alkyl]carbamoyl-(1–4C)alkoxy-(2–4C)alkoxy:
2-[N-{2-(2-hydroxyethyl)aminoethyl}carbamoylmethoxy]ethoxy and 3-[N-{2-(2-hydroxyethyl)aminoethyl}carbamoylmethoxy]propoxy;

for N-[N-{hydroxy-(2–4C)alkyl}-N-{(1–4C)alkyl}amino-(2–4C)alkyl]carbamoyl-(1–4C)alkoxy-(2–4C)alkoxy:
2-(N-[2-{N-(2-hydroxyethyl)-N-methylamino}ethyl]carbamoylmethoxy)ethoxy and 3-(N-[2-{N-(2-hydroxyethyl)-N-methylamino}ethyl]carbamoylmethoxy)propoxy;

for N-[N,N-di-{hydroxy-(2–4C)alkyl}amino-(2–4C)alkyl]carbamoyl-(1–4C)alkoxy-(2–4C)alkoxy:
2-(N-[2-{di-(2-hydroxyethyl)amino}ethyl]carbamoylmethoxy)ethoxy and 3-(N-[2-{di-(2-hydroxyethyl)amino}ethyl]carbamoylmethoxy)propoxy;

for (2–4C)alkanoyloxy:
acetoxy, propionyloxy and butyryloxy;

for N-[hydroxy-(2–4C)alkyl]amino:
N-(2-hydroxyethyl)amino and N-(3-hydroxypropyl)amino;

for N-[hydroxy-(2–4C)alkyl]N-[(1–4C)alkyl]amino:
N-(2-hydroxyethyl)-N-methylamino and N-(3-hydroxypropyl)-N-ethylamino;

for (1–4C)alkylsulphonylamino:
methylsulphonylamino, ethylsulphonylamino and propylsulphonylamino.

When $R^1$ or $R^2$ is (1–3C)alkylenedioxy the oxygen atoms of each such group occupy adjacent positions on the anilino ring.

A suitable value for $R^2$ when it is (2–4C)alkanoyl is, for example, acetyl, propionyl or butyryl.

A suitable pharmaceutically-acceptable salt of a pyrimidine derivative of the invention is, for example, an acid-addition salt of a pyrimidine derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a pyrimidine derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention include, for example, pyrimidine derivatives of the formula I, or pharmaceutically-acceptable salts thereof wherein:

(a) m is 1 or 2 and each $R^1$ is independently hydrogen, hydroxy, amino, halogeno, cyano, (1–4C)alkyl, (1–4C)alkoxy, (1–3C)alkylenedioxy, (1–4C)alkylamino, di-[(1–4C)alkyl]amino, hydroxy-(2–4C)alkoxy or (1–4C)alkoxy-(2–4C)alkoxy; and n and $R^2$ have any of the meanings defined hereinbefore or in this section relating to particular novel compounds of the invention;

(b) m is 1, 2 or 3 and each $R^1$ is independently hydrogen, hydroxy, amino, halogeno, cyano, carboxy, carbamoyl, ureido, (1–4C)alkoxycarbonyl, (1–4C)alkyl, (1–4C)alkoxy, (1–3C)alkylenedioxy, (1–4C)alkylamino, di-[(1–4C)alkyl]amino, (1–4C)alkylthio, halogeno-(1–4C)alkyl, (1–4C)alkoxy-(1–4C)alkyl, (1–4C)alkylamino-(1–4C)alkyl, di-[(1–4C)alkyl]amino-(1–4C)alkyl, cyano-(1–4C)alkyl, halogeno-(1–4C)alkoxy, hydroxy-(2–4C)alkoxy, (1–4C)alkoxy-(2–4C)alkoxy, (1–4C)alkoxycarbonyl-(1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, (1–4C)alkylamino-(2–4C)alkoxy, di-[(1–4C)alkyl]amino-(2–4C)alkoxy or (2–4C)alkanoylamino; and n and $R^2$ have any of the meanings defined hereinbefore or in this section relating to particular novel compounds of the invention; except that 4,6-di-(3'-trifluoromethylanilino)-pyrimidine is excluded;

(c) m is 1, 2 or 3 and each $R^1$ is independently hydrogen, hydroxy, amino, halogeno, cyano, carboxy, carbamoyl, ureido, (1–4C)alkoxycarbonyl, (1–4C)alkyl, (1–4C)alkoxy, (1–3C)alkylenedioxy, (1–4C)alkylamino, di-[(1–4C)alkyl]amino, (1–4C)alkylthio, halogeno-(1–4C)alkyl, (1–4C)alkoxy-(1–4C)alkyl, (1–4C)alkylamino-(1–4C)alkyl, di-[(1–4C)alkyl]amino-(1–4C)alkyl, cyano-(1–4C)alkyl, halogeno-(1–4C)alkoxy, hydroxy-(2–4C)alkoxy, (1–4C)alkoxy-(2–4C)alkoxy, (1–4C)alkoxycarbonyl-(1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C) alkoxy, N-[hydroxy-(2–4C)alkyl]carbamoyl-(1–4C) alkoxy, N,N-di-[hydroxy-(2–4C)alkyl]carbamoyl-(1–4C)alkoxy, (1–4C)alkylamino-(2–4C)alkoxy, di-[(1–4C)alkyl]amino-(2–4C)alkoxy, (2–4C)alkanoylamino, N-[hydroxy-(2–4C)alkyl]amino, N-[hydroxy-(2–4C)alkyl]N-[(1–4C)alkyl]amino, (1–4C)alkylamino-hydroxy-(2–4C)alkoxy, di-[(1–4C)alkyl]amino-hydroxy-(2–4C)alkoxy, N-[amino-(2–4C)alkyl]carbamoyl-(1–4C)alkoxy, N-[N-{(1–4C)alkyl}amino-(2–4C)alkyl]carbamoyl-(1–4C)alkoxy or N-[N,N-di-{(1–4C)alkyl}amino-(2–4C)alkyl]carbamoyl-(1–4C)alkoxy; and n and $R^2$ have any of the the meanings defined hereinbefore or in this section relating to particular novel compounds of the invention; except that 4,6-di-(3'-trifluoromethylanilino)pyrimidine is excluded;

(d) m is 1 or 2 and each $R^1$ is independently hydrogen, hydroxy, amino, halogeno, cyano, carboxy, carbamoyl, ureido, (1–4C)alkoxycarbonyl, (1–4C)alkyl, (1–4C)alkoxy, (1–3C)alkylenedioxy, (1–4C)alkylamino, di-[(1–4C)alkyl]amino, halogeno-(1–4C)alkyl, cyano-(1–4C)alkyl, halogeno-(1–4C)alkoxy, hydroxy-(2–4C)alkoxy, (1–4C)alkoxy-(2–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, N-[hydroxy-(2–4C)alkyl]carbamoyl-(1–4C)alkoxy, N,N-di-[hydroxy-(2–4C)alkyl]carbamoyl-(1–4C)alkoxy, (1–4C)alkylamino-(2–4C)alkoxy, di-[(1–4C)alkyl]amino-(2–4C)alkoxy, (2–4C)alkanoylamino, N-[hydroxy-(2–4C)alkyl]amino, N-[hydroxy-(2–4C)alkyl]N-[(1–4C)alkyl]amino, (1–4C)alkylamino-hydroxy-(2–4C)alkoxy, di-[(1–4C)alkyl]amino-hydroxy-(2–4C)alkoxy, N-[amino-(2–4C)alkyl]carbamoyl-(1–4C)alkoxy, N-[N-{(1–4C)alkyl}amino-(2–4C)alkyl]carbamoyl-(1–4C)alkoxy or N-[N,N-di-{(1–4C)alkyl}amino-(2–4C)alkyl]carbamoyl-(1–4C)alkoxy; and n and $R^2$ have any of the meanings defined hereinbefore or in this section relating to particular novel compounds of the invention except that 4,6-di-(3'-trifluoromethylanilino)pyrimidine is excluded;

(e) m is 1, 2 or 3 and each $R^1$ is independently hydrogen, hydroxy, amino, halogeno, cyano, carboxy, carbamoyl, ureido, (1–4C)alkoxycarbonyl, (1–4C)alkyl, (1–4C)alkoxy, (1–3C)alkylenedioxy, (1–4C)alkylamino, di-[(1–4C)alkyl]amino, (1–4C)alkylthio, halogeno-(1–4C)alkyl, (1–4C)alkoxy-(1–4C)alkyl, (1–4C)alkylamino-(1–4C)alkyl, di-[(1–4C)alkyl]amino-(1–4C)alkyl, cyano-(1–4C)alkyl, halogeno-(1–4C)alkoxy, hydroxy-(2–4C)alkoxy, (1–4C)alkoxy-(2–4C)alkoxy, (1–4C)alkoxycarbonyl-(1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, N-[hydroxy-(2–4C) alkyl]carbamoyl-(1–4C)alkoxy, N,N-di-[hydroxy-(2–4C)alkyl]carbamoyl-m(4–4C)alkoxy, (1–4C)alkylamino-(2–4C)alkoxy, di-[(1–4C)alkyl]amino-(2–4C)alkoxy, (2–4C)alkanoylamino, N-[hydroxy-(2–4C)alkyl]amino, N-[hydroxy-(2–4C)alkyl]N-[(1–4C)alkyl]amino, (1–4C)alkylamino-hydroxy-(2–4C)alkoxy, di-[(1–4C)alkyl]amino-hydroxy-(2–4C)alkoxy, N-[amino-(2–4C)alkyl]carbamoyl-(1–4C)alkoxy, N-[N-{(1–4C)alkyl]carbamoyl-(1–4C)alkoxy, N-[N-{(1–4C)alkyl}amino-(2–4C)alkyl]carbamoyl-(1–4C)alkoxy or N-[N,N-di-{(1–4C)alkyl}amino-(2–4C)alkyl]carbamoyl-(1–4C)alkoxy;

n is 1, 2 or 3 and each $R^2$ is independently hydrogen, hydroxy, halogeno, trifluoromethyl, trifluoromethoxy, amino, nitro, cyano, (1–4C)alkyl, (1–4C)alkoxy, (1–4C)alkylamino, di-[(1–4C)alkyl]amino, (1–4C)alkylthio or (2–4C)alkanoylamino; except that 4,6-di-(3'-trifluoromethylanilino)pyrimidine is excluded.

(f) m is 1 or 2 and each $R^1$ is independently hydrogen, hydroxy, amino, halogeno, cyano, carboxy, carbamoyl, ureido, (1–4C)alkoxycarbonyl, (1–4C)alkyl, (1–4C)alkoxy, (1–3C)alkylenedioxy, (1–4C)alkylamino, di-[(1–4C)alkyl]amino, halogeno-(1–4C)alkyl, cyano-(1–4C)alkyl, halogeno-(1–4C)alkoxy, hydroxy-(2–4C)alkoxy, (1–4C)alkoxy-(2–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, N-[hydroxy-(2–4C)alkyl]carbamoyl-(1–4C)alkoxy, N,N-di-[hydroxy-(2–4C)alkyl]carbamoyl-(1–4C)alkoxy, (1–4C)alkylamino-(2–4C)alkoxy, di-[(1–4C)alkyl]amino-(2–4C)alkoxy, (2–4C)alkanoylamino, N-[hydroxy-(2–4C)alkyl]amino, N-[hydroxy-(2–4C)alkyl]N-[(1–4C)alkyl]amino, (1–4C)alkylamino-hydroxy-(2–4C)alkoxy, di-[(1–4C)alkyl]amino-hydroxy-(2–4C)alkoxy, N-[amino-(2–4C)alkyl]carbamoyl-(1–4C)alkoxy, N-[N-{(1–4C)alkyl}amino-(2–4C)alkyl]carbamoyl-(1–4C)alkoxy or N-[N,N-di-{(1–4C)alkyl}amino-(2–4C)alkyl]carbamoyl-(1–4C)alkoxy;

n is 1, 2 or 3 and each $R^2$ is independently hydrogen, hydroxy, halogeno, trifluoromethyl, trifluoromethoxy, amino, nitro, cyano, (1–4C)alkyl, (1–4C)alkoxy, (1–4C)alkylamino, di-[(1–4C)alkyl]amino, (1–4C)alkylthio or (2–4C)alkanoylamino; except that 4,6-di-(3'-trifluoromethylanilino)-pyrimidine is excluded;

(g) m is 1 or 2 and each $R^1$ is independently hydrogen, hydroxy, amino, halogeno, cyano, carboxy, carbamoyl, ureido, (1–4C)alkoxycarbonyl, (1–4C)alkyl, (1–4C)alkoxy, (1–3C)alkylenedioxy, (1–4C)alkylamino, di-[(1–4C)alkyl]amino, halogeno-(1–4C)alkyl, cyano-(1–4C)alkyl, halogeno-(1–4C)alkoxy, hydroxy-(2–4C)alkoxy, (1–4C)alkoxy-(2–4C)alkoxy, carbamoyl-(1–4C)alkoxy or (2–4C)alkanoylamino; and n and $R^2$ have any of the meanings defined hereinbefore or in this section relating to particular novel compounds of the invention; except that 4,6-di-(3'-trifluoromethylanilino)pyrimidine is excluded; or (h) n is 1 or 2 and each $R^2$ is independently hydrogen, hydroxy, halogeno, trifluoromethyl, trifluoromethoxy, nitro, cyano, (1–4C)alkyl, (1–4C)alkoxy or (1–4C)alkylthio; and m and $R^1$ have any of the meanings defined hereinbefore or in this section relating to particular novel compounds of the invention; except that 4,6-di-(3'-trifluoromethylanilino) pyrimidine is excluded.

A preferred compound of the invention is a pyrimidine derivative of the formula I wherein m is 1 or 2 and each $R^1$ is independently hydrogen, hydroxy, amino, fluoro, chloro, bromo, trifluoromethyl, trifluoromethoxy, cyano, methyl, ethyl, methoxy, ethoxy, methylenedioxy, methylamino, ethylamino, dimethylamino, diethylamino, 2-hydroxyethoxy, 3-hydroxypropoxy, 2-methoxyethoxy, 2-ethoxyethoxy, 3-methoxypropoxy, methoxycarbonylmethoxy, ethoxycarbonylmethoxy, cyanomethoxy, carbamoylmethoxy, N-methylcarbamoylmethoxy, N,N-dimethylcarbamoylmethoxy, 2-(methylamino)ethoxy, 2-(ethylamino)ethoxy, 3-(methylamino)propoxy, 3-(ethylamino)propoxy, 2-(dimethylamino)ethoxy, 2-(diethylamino)ethoxy, 3-(dimethylamino)propoxy, 3-(diethylamino)propoxy, acetamido, N-(2-hydroxyethyl)carbamoylmethoxy, 2-[N-(2-hydroxyethyl)carbamoyl]methoxy, N,N-di-(2-hydroxyethyl)carbamoylmethoxy, 2-[N,N-di-(2-hydroxyethyl)carbamoyl]ethoxy, N-(2-hydroxyethyl)amino, N-(3-hydroxypropyl)amino, N-(2-hydroxyethyl)-N-methylamino, N-(3-hydroxypropyl)-N-ethylamino, 3-amino-2-hydroxypropoxy, 3-methylamino-2-hydroxypropoxy, 3-dimethylamino-2-hydroxypropoxy, N-(2-aminoethyl)carbamoylmethoxy, 2-[N-(2-aminoethyl)carbamoyl]ethoxy, N-(2-methylaminoethyl)carbamoylmethoxy, 2-[N-(2-methylaminoethyl)carbamoyl]ethoxy, N-(2-dimethylaminoethyl)carbamoylmethoxy or 2-[N-(2-dimethylaminoethyl)carbamoyl]ethoxy; and n is 1 or 2 and each $R^2$ is independently hydrogen, hydroxy, fluoro, chloro, bromo, trifluoromethyl, trifluoromethoxy, cyano, methyl, ethyl, methoxy or ethoxy;

or a pharmaceutically-acceptable salt thereof;

except that 4,6-di-(3'-trifluoromethylanilino)pyrimidine is excluded.

A further preferred compound of the invention is a pyrimidine derivative of the formula I wherein m is 1 or 2 and each $R^1$ is independently hydrogen, hydroxy, amino, fluoro, chloro, bromo, trifluoromethyl, trifluoromethoxy, cyano, methyl, ethyl, methoxy, ethoxy, methylenedioxy, methylamino, ethylamino, dimethylamino, diethylamino, 2-hydroxyethoxy, 3-hydroxypropoxy, 2-methoxyethoxy, 2-ethoxyethoxy, 3-methoxypropoxy, methoxycarbonylmethoxy, ethoxycarbonylmethoxy, cyanomethoxy, carbamoylmethoxy, N-methylcarbamoylmethoxy, N,N-dimethylcarbamoylmethoxy, 2-(methylamino)ethoxy, 2-(ethylamino)ethoxy, 2-(dimethylamino)ethoxy, 2-(diethylamino)ethoxy or acetamido; and n is 1 or 2 and each $R^2$ is independently hydrogen, hydroxy, fluoro, chloro, bromo, trifluoromethyl, trifluoromethoxy, cyano, methyl, ethyl, methoxy or ethoxy;

or a pharmaceutically-acceptable salt thereof; except that 4,6-di-(3'-trifluoromethylanilino)pyrimidine is excluded.

A further preferred compound of the invention is a pyrimidine derivative of the formula I wherein m is 1 or 2 and each $R^1$ is independently hydrogen, hydroxy, fluoro, chloro, methyl, methoxy, dimethylamino, 2-hydroxyethoxy, 3-hydroxypropoxy, 2-methoxyethoxy, methoxycarbonylmethoxy, ethoxycarbonylmethoxy, cyanomethoxy, carbamoylmethoxy, N-methylcarbamoylmethoxy, N,N-dimethylcarbamoylmethoxy, 2-(dimethylamino)ethoxy, 3-(dimethylamino)propoxy, N-(2-hydroxyethyl)carbamoylmethoxy, N,N-di-(2-hydroxyethyl)carbamoylmethoxy, N-(2-hydroxyethyl)-N-methylamino, 3-methylamino-2-hydroxypropoxy, 3-dimethylamino-2-hydroxypropoxy or N-(2-dimethylaminoethyl)carbamoylmethoxy; and n is 1 or 2 and each $R^2$ is independently fluoro, chloro, bromo-, trifluoromethyl, methyl or ethyl;

or a pharmaceutically-acceptable acid-addition salt thereof.

A further preferred compound of the invention is a pyrimidine derivative of the formula I wherein m is 1 or 2 and each $R^1$ is independently hydrogen, hydroxy, fluoro, chloro, methyl, methoxy, methylenedioxy, 2-hydroxyethoxy, 2-methoxyethoxy, methoxycarbonylmethoxy, ethoxycarbonylmethoxy, cyanomethoxy, N-methylcarbamoylmethoxy or N,N-dimethylcarbamoylmethoxy; and n is 1 or 2 and each $R^2$ is independently fluoro, chloro, bromo, trifluoromethyl, methyl or ethyl;

or a pharmaceutically-acceptable acid-addition salt thereof.

A further prefered compound of the invention is a pyrimidine derivative of the formula I wherein m is 1 and $R^1$ is independently hydrogen, hydroxy, fluoro, chloro, methyl, methoxy, dimethylamino, 2-hydroxyethoxy, 3-hydroxypropoxy, 2-methoxyethoxy, methoxycarbonylmethoxy, ethoxycarbonylmethoxy, cyanomethoxy, carbamoylmethoxy, N-methylcarbamoylmethoxy, N,N-dimethylcarbamoylmethoxy, 2-dimethylaminoethoxy, 3-dimethylaminopropoxy, N-(2-hydroxyethyl)carbamoylmethoxy, N,N-di-(2-hydroxyethyl)carbamoylmethoxy, N-(2-hydroxyethyl)-N-methylamino, 3-methylamino-2-hydroxypropoxy, 3-dimethylamino-2-hydroxypropoxy or N-(2-dimethylaminoethyl)carbamoylmethoxy; and n is 1 or 2 and each $R^2$ is independently fluoro, chloro or methyl;

or a pharmaceutically-acceptable acid-addition salt thereof.

A further preferred compound of the invention is a pyrimidine derivative of the formula I wherein m is 1 and $R^1$ is hydrogen, chloro, methyl, methoxy, dimethylamino or 2-hydroxyethoxy; and n is 1 or 2 and each $R^2$ is independently fluoro, chloro or methyl; or a pharmaceutically-acceptable acid-addition salt thereof.

A specific preferred compound of the invention is the following pyrimidine derivative of the formula I:

4-(3'-chloro-4'-fluoroanilino)-6-(4'-methoxyanilino)pyrimidine, 4-(3'-chloro-4'-fluoroanilino)-6-(4'-dimethylaminoanilino)pyrimidine, 4-(3'-chloro-4'-fluoroanilino)-6-[4'-(2-hydroxyethoxy)anilino]pyrimidine, 4-(3'-chloro-4'-fluoroanilino)-6-(4'-methylanilino)pyrimidine, 4,6-di-(3'-methylanilino)pyrimidine, 4-[4'-(carbamoylmethoxy)anilino]6-(3'-chloro-4'-fluoroanilino)pyrimidine, 4-(3'-chloro-4'-fluoroanilino)-6-[4'-(N,N-dimethylcarbamoylmethoxy)anilino]pyrimidine, 4-[4'-(2-hydroxyethoxy)anilino]6-(3'-methylanilino)pyrimidine, 4-[4'-(2-dimethylaminoethoxy)anilino]6-(3'-methylanilino)pyrimidine, 4-[4'-(3-dimethylaminopropoxy)anilino]6-(3'-methylanilino)pyrimidine, 4-(3'-chloro-4'-fluoroanilino)-6-[4'-{N-(2-hydroxyethyl)carbamoylmethoxy}anilino]pyrimidine, 4-[4'-{N-(2-dimethylaminoethyl)carbamoylmethoxy}anilino]6-(3'-methylanilino)pyrimidine or 4-[4'-(3-dimethylamino-2-hydroxypropoxy)anilino]6-(3'-methylanilino)pyrimidine;

or a pharmaceutically-acceptable acid-addition salt thereof.

A further specific preferred compound of the invention is the following pyrimidine derivative of the formula I:

4-(3'-chloro-4'-fluoroanilino)-6-(4'-methoxyanilino) pyrimidine,
4-(3'-chloro-4'-fluoroanilino)-6-(4'-dimethylaminoanilino) pyrimidine,
4-(3'-chloro-4'-fluoroanilino)-6-[4'-(2-hydroxyethoxy) anilino]pyrimidine,
4-(3'-chloro-4'-fluoroanilino)-6-(4'-methylanilino) pyrimidine or
4,6-di-(3'-methylanilino)pyrimidine;
or a pharmaceutically-acceptable acid-addition salt thereof.

A pyrimidine derivative of the formula I, or a pharmaceutically-acceptable salt thereof, may be prepared by any process known to be applicable to the preparation of chemically-related compounds. Such processes, when used to prepare a pyrimidine derivative of the formula I, or a pharmaceutically-acceptable salt thereof, are provided as a further feature of the invention and are illustrated by the following representative examples in which, unless otherwise stated, $R^1$, m, n and $R^2$ have any of the meanings defined hereinbefore for a pyrimidine derivative of the formula I. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

(a) The reaction, conveniently in the presence of a suitable base, of a pyrimidine of the formula II

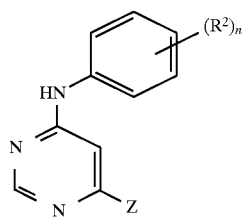

wherein Z is a displaceable group, with an aniline of the formula III

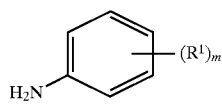

A suitable displaceable group Z is, for example, a halogeno, alkoxy, aryloxy or sulphonyloxy group, for example a chloro, bromo, methoxy, phenoxy, methane-sulphonyloxy or toluene-p-sulphonyloxy group.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

The reaction is conveniently carried out in the absence of a suitable inert solvent or diluent. Alternatively the reaction is conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethyl-sulphoxide. The reaction is conveniently carried out at a temperature in the range, for example, 10° to 250° C., preferably in the range 100°–200° C.

The pyrimidine derivative of the formula I may be obtained from this process in the form of the free base or alternatively it may be obtained in the form of a salt with the acid of the formula H—Z wherein Z has the meaning defined hereinbefore. When it is desired to obtain the free base from the salt, the salt may be treated with a suitable base as defined hereinbefore using a conventional procedure.

(b) The reaction, conveniently in the presence of a suitable base as defined hereinbefore, of a pyrimidine of the formula IV

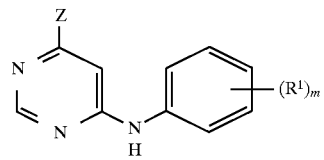

wherein Z is a displaceable group as defined hereinbefore, with an aniline of the formula V

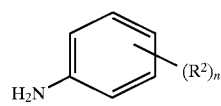

The reaction is conveniently carried out in the presence or absence of a suitable inert solvent or diluent as defined hereinbefore and at a temperature in the range, for example, 10° to 250° C., preferably in the range 100°–200° C.

(c) For the production of those compounds of the formula I wherein each of m and n and each of $R^1$ and $R^2$ have the same definition, the reaction, conveniently in the presence of a suitable base as defined hereinbefore, of a pyrimidine of the formula VI

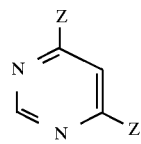

wherein Z is a displaceable group as defined hereinbefore, with an aniline of the formula III.

The reaction is conveniently carried out in the presence or absence of a suitable inert solvent or diluent as defined hereinbefore and at a temperature in the range, for example, 10° to 250° C., preferably in the range 100° to 200° C.

(d) For the production of those compounds of the formula I wherein $R^1$ or $R^2$ is a (1–4C)alkylsulphinyl or (1–4C) alkylsulphonyl group, the oxidation of a pyrimidine derivative of the formula I wherein $R^1$ or $R^2$ is a (1–4C)alkylthio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, −25° to 50° C., conveniently at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a (1–4C)alkylsulphonyl group is required, it may be obtained by oxidation of the corresponding (1–4C) alkylsulphinyl compound as well as of the corresponding (1–4C)alkylthio compound.

(e) For the production of those compounds of the formula I wherein $R^1$ or $R^2$ is amino, the reduction of a pyrimidine derivative of the formula I wherein $R^1$ or $R^2$ is nitro.

The reduction may conveniently be carried out by any of the many procedures known for such a transformation. The reduction may be carrried out, for example, by the hydrogenation of a solution of the nitro compound in an inert solvent or diluent as defined hereinbefore in the presence of a suitable metal catalyst such as palladium or platinum. A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal in a suitable solvent or diluent such as a mixture of water and an alcohol, for example, methanol or ethanol, to a temperature in the range, for example, 50° to 150° C., conveniently at or near 70° C.

(f) For the production of those compounds of the formula I wherein $R^1$ or $R^2$ is (2–4C)alkanoylamino, the acylation of a pyrimidine derivative of the formula I wherein $R^1$ or $R^2$ is amino.

A suitable acylating agent is, for example, any agent known in the art for the acylation of amino to acylamino, for example an acyl halide, for example a (2–4C)alkanoyl chloride or bromide or a benzoyl chloride or bromide, conveniently in the presence of a suitable base, as defined hereinbefore, an alkanoic acid anhydride or mixed anhydride, for example a (2–4C)alkanoic acid anhydride such as acetic anhydride or the mixed anhydride formed by the reaction of an alkanoic acid and a (1–4C)alkoxycarbonyl halide, for example a (1–4C)alkoxycarbonyl chloride, in the presence of a suitable base as defined hereinbefore. In general the acylation is carried out in a suitable inert solvent or diluent as defined hereinbefore and at a temperature, in the range, for example, −30° to 120° C., conveniently at or near ambient temperature.

(g) For the production of those compounds of the formula I wherein $R^1$ is (1–4C)alkoxy or substituted alkoxy or $R^2$ is (1–4C)alkoxy, the alkylation, preferably in the presence of a suitable base as defined hereinbefore, of a pyrimidine derivative of the formula I wherein $R^1$ or $R^2$ is hydroxy.

A suitable alkylating agent is, for example, any agent known in the art for the alkylation of hydroxy to alkoxy or substituted alkoxy for example an alkyl or substituted alkyl halide, for example a (1–4C)alkyl chloride, bromide or iodide or a substituted (1–4C)alkyl chloride, bromide or iodide, in the presence of a suitable base as defined hereinbefore, in a suitable inert solvent or diluent as defined hereinbefore and at a temperature in the range, for example, 10° to 140° C., conveniently at or near ambient temperature.

(h) For the production of those compounds of the formula I wherein $R^1$ is a carboxy substituent or a substituent which includes a carboxy group, the hydrolysis of a pyrimidine derivative of the formula I wherein $R^1$ is a (1–4C) alkoxycarbonyl substituent or a substituent which includes a (1–4C)alkoxycarbonyl group.

The hydrolysis may conveniently be performed, for example, under basic conditions.

(i) For the production of those compounds of the formula I wherein $R^1$ is an amino-, oxy- or cyano-substituted (1–4C) alkyl substituent, the reaction, preferably in the presence of a suitable base as defined hereinbefore, of a pyrimidine derivative of the formula I wherein $R^1$ is a (1–4C)alkyl substituent bearing a displaceable group as defined hereinbefore with an appropriate amine, alcohol or cyanide.

The reaction is preferably carried out in a suitable inert solvent or diluent as defined hereinbefore and at a temperature in the range, for example, 10° to 100° C., conveniently at or near ambient temperature.

(j) For the production of those compounds of the formula I wherein $R^1$ is a carbamoyl substituent, or a substituent which contains a carbamoyl group or a substituted carbamoyl group, the reaction of a pyrimidine derivative of the formula I wherein $R^1$ is an acid group or a reactive derivative thereof, or a substituent which contains an acid group or a reactive derivative thereof, with ammonia or an appropriate amine.

A suitable reactive derivative of an acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction is conveniently performed, for example, in an alkanol solvent, such as methanol, ethanol or isopropanol, conveniently at the reflux temperature of the alkanol.

(k) For the production of those compounds of the formula I wherein $R^1$ is a substituent containing an ethanolamine moiety, the reaction of a pyrimidine derivative of the formula I wherein $R^1$ is a substituent containing an epoxide group, with ammonia or an appropriate amine.

The reaction is conveniently carried out in a suitable solvent, for example an alkanol such as methanol, ethanol or isopropanol, or a mixture of an alkanol and an inert solvent or diluent as defined hereinbefore. The reaction is conveniently carried out at a temperature at or near ambient temperature.

When a pharmaceutically-acceptable salt of a pyrimidine derivative of the formula I is required, for example an acid-addition salt, it may be obtained, for example, by reaction of said compound with, for example, a suitable acid using a conventional procedure.

Many of the intermediates defined herein are novel, for example, those of the formula II and IV and these are provided as a further feature of the invention.

As stated hereinbefore the pyrimidine derivative defined in the present invention possesses anti-cell-proliferation activity such as anti-cancer activity which is believed to arise from the Class I receptor tyrosine kinase inhibitory activity of the compound. These properties may be assessed, for example, using one or more of the procedures set out below:

(a) An in vitro assay which determines the ability of a test compound to inhibit the enzyme EGF receptor tyrosine kinase. Receptor tyrosine kinase was obtained in partially purified form from A-431 cells (derived from human vulval carcinoma) by procedures related to those described by Carpenter et al., *J. Biol. Chem.*, 1979, 254, 4884, Cohen et al., *J. Biol. Chem.*, 1982, 257, 1523 and by Braun et al., *J. Biol. Chem.*, 1984, 259, 2051.

A-431 cells were grown to confluence using Dulbecco's modified Eagle's medium (DMEM) containing 5% fetal calf serum (FCS). The obtained cells were homogenised in a hypotonic borate/EDTA buffer at pH 10.1. The homogenate was centrifuged at 400 g for 10 minutes at 0°–4° C. The supernatant was centrifuged at 25,000 g for 30 minutes at 0°–4° C. The pelleted material was suspended in 30 mM Hepes buffer at pH 7.4 containing 5% glycerol, 4 mM benzamidine and 1% Triton X-100, stirred for 1 hour at 0°–40° C., and recentrifuged at 100,000 g for 1 hour at 0°–40C. The supernatant, containing solubilised receptor tyrosine kinase, was stored in liquid nitrogen.

For test purposes 40 μl of the enzyme solution so obtained was added to a mixture of 400 μl of a mixture of 150 mM Hepes buffer at pH 7.4, 500 μM sodium orthovanadate, 0.1% Triton X-100, 10% glycerol, 200 μl water, 80 μl of 25 mM DTT and 80 μl of a mixture of 12.5 mM manganese chloride, 125 mM magnesium chloride and distilled water. There was thus obtained the test enzyme solution.

Each test compound was dissolved in dimethylsulphoxide (DMSO) to give a 50 mM solution which was diluted with 40 mM Hepes buffer containing 0.1% Triton X-100, 10% glycerol and 10% DMSO to give a 500 μM solution. Equal volumes of this solution and a solution of epidermal growth factor (EGF; 20 pg/ml) were mixed.

[$\gamma$-$^{32}$ P]ATP (3000 Ci/mM, 250 μCi) was diluted to a volume of 2 ml by the addition of a solution of ATP (100 μM) in distilled water. An equal volume of a 4 mg/ml solution of the peptide Arg-Arg-Leu-Ile-Glu-Asp-Ala-Glu-Tyr-Ala-Ala-Arg-Gly in a mixture of 40 mM Hepes buffer at pH 7.4, 0.1% Triton X-100 and 10% glycerol was added.

The test compound/EGF mixture solution (5 μl) was added to the test enzyme solution (10 μl) and the mixture was incubated at 0–4° C. for 30 minutes. The ATP/peptide mixture (10 μl) was added and the mixture was incubated at 25° C. for 10 minutes. The phosphorylation reaction was terminated by the addition of 5% trichloroacetic acid (40 μl) and bovine serum albumin (BSA; 1 mg/ml, 5 μl). The mixture was allowed to stand at 4° C. for 30 minutes and then centrifuged. An aliquot (40 μl) of the supernatant was placed onto a strip of Whatman p 81 phosphocellulose paper. The strip was washed in 75 mM phosphoric acid (4×10 ml) and blotted dry. Radioactivity present in the filter paper was measured using a liquid scintillation counter (Sequence A). The reaction sequence was repeated in the absence of the EGF (Sequence B) and again in the absence of the test compound (Sequence C).

Receptor tyrosine kinase inhibition was calculated as follows:

$$\% \text{ Inhibition} = \frac{100 - (A - B)}{C - B} \times 100$$

The extent of inhibition was then determined at a range of concentrations of test compound to give an $IC_{50}$ value.

(b) An in vitro assay which determines the ability of a test compound to inhibit the EGF-stimulated growth of the human naso-pharyngeal cancer cell line KB.

KB cells were seeded into wells at a density of $1 \times 10^4$–$1.5 \times 10^4$ cells per well and grown for 24 hours in DMEH supplemented with 5% FCS (charcoal-stripped). Cell growth was determined after incubation for 3 days by the extent of metabolism of MTT tetrazolium dye to furnish a bluish colour. Cell growth was then determined in the presence of EGF (10 ng/ml) or in the presence of EGF (10 ng/ml) and a test compound at a range of concentrations. An $IC_{50}$ value could then be calculated.

(c) An in vivo assay in a group of male rats which determines the ability of a test compound (usually administered orally as a ball-milled suspension in 0.5% polysorbate) to inhibit the stimulation of liver hepatocyte growth caused by the administration of the growth factor TGFα (400 μg/kg subcutaneously, usually dosed twice, 3 and 7 hours respectively after the administration of the test compound).

In a control group of rats, the administration of TGFα causes on average a 5-fold stimulation of liver hepatocyte growth.

Cell-growth in the control and test animals is determined as follows:

On the morning of the day after the dosing of the test compound (or 0.5% polysorbate in the control group), the animals are dosed with bromodeoxyuridine (BrdU; 100 mg/kg intraperitoneally). The animals are killed four hours later and the livers are excised. Slices are cut from each liver and the uptake of BrdU is determined by a conventional immunohistochemical technique similar to that described on pages 267 and 268 of an article by Goldsworthy et al. in Chemically Induced Cell Proliferation: Implications for Risk Assessment, Wiley-Liss Inc., 1991, pages 253–284. Further tests were carried out using a range of doses of the test compounds to allow the calculation of an approximate $ED_{50}$ value for the inhibition of liver hepatocyte proliferation as determined by inhibition of the uptake of BrdU.

Although the pharmacological properties of the compounds of the formula I vary with structural change as expected, in general activity possessed by compounds of the formula I may be demonstrated at the following concentrations or doses in one or more of the above tests (a), (b) and (c):

Test (a): $IC_{50}$ in the range, for example, 0.01–1 μM;
Test (b): $IC_{50}$ in the range, for example, 0.1–10 μM;
Test (c): $ED_{50}$ in the range, for example, 1–100 mg/kg.

Thus, by way of example, the compound 4,6-di-(3'-methylanilino)pyrimidine has an $IC_{50}$ of 0.24 μM in Test (a), an $IC_{50}$ of 1.1 μM in Test (b) and an $ED_{50}$ of <12.5 mg/kg in Test (c); 4-[4'-(2-hydroxyethoxy)anilino]6-(3'-methylanilino)pyrimidine has an $IC_{50}$ of 0.001 μM in Test (a), an $IC_{50}$ of 1.07 μM in Test (b) and an $ED_{50}$ of <12.5 mg/kg in Test (c), and 4-[4'-(3-dimethylamino-2-hydroxypropoxy)anilino]6-(3'-methylanilino)pyrimidine has an $IC_{50}$ of 0.01 μM in Test (a) and-an IC50 of 0.31 μM in Test (b).

According to a further aspect of the invention there is provided a pharmaceutical composition which comprises a pyrimidine derivative of the formula I, or a pharmaceutically-acceptable salt thereof, as defined hereinbefore in association with a pharmaceutically-acceptable diluent or carrier.

The composition may be in a form suitable for oral administration, for example as a tablet or capsule,for parenteral injection (including intraveous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The pyrimidine will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a pyrimidine derivative of the formula I as defined hereinbefore for use in a method of treatment of the human or animal body by therapy.

We have now found that the compounds of the present invention possess anti-cell-proliferation properties which are believed to arise from their Class I receptor tyrosine kinase inhibitory activity. Accordingly the compounds of the present invention are expected to be useful in the treatment of diseases or medical conditions mediated alone or in part by Class I receptor tyrosine kinase enzymes, i.e. the compounds may be used to produce a Class I receptor tyrosine kinase inhibitory effect in a warm-blooded animal in need of such treatment. Thus the compounds of the present invention provide a method for treating the proliferation of malignant cells characterised by inhibition of Class I receptor tyrosine kinase enzymes, i.e. the compounds may be used to produce an anti-proliferative effect mediated alone or in part by the inhibition of Class I receptor tyrosine kinase. Accordingly the compounds of the present invention are expected to be useful in the treatment of cancer by providing an anti-proliferative effect, particularly in the treatment of Class I receptor tyrosine kinase sensitive cancers such as cancers of the breast, lung; colon, rectum, stomach, prostate, bladder, pancreas and ovary. It is further expected that a pyrimidine derivative of the present invention will possess activity against other cell-proliferation diseases such as psoriasis.

Thus according to this aspect of the invention there is provided the use of a pyrimidine derivative of the formula I, or a pharmaceutically-acceptable salt thereof, as defined hereinbefore in the manufacture of a medicament for use in the production of an anti-cell-proliferation effect in a warm-blooded animal such as man.

According to a further feature of this aspect of the invention there is provided a method for producing an anti-cell-proliferation effect in a warm-blooded animal, such as man, in need of such treatment which comprises administering to said animal an effective amount of a pyrimidine derivative as defined immediately above.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The anti-cell-proliferation treatment defined hereinbefore may be applied as a sole therapy or may involve, in addition to the pyrimidine derivative of the invention, one or more other anti-tumour substances, for example those selected from, for example, mitotic inhibitors, for example vinblastine; alkylating agents, for example cis-platin, carboplatin and cyclophosphamide; antimetabolites, for example 5-fluorouracil, cytosine arabinoside and hydroxyurea, or, for example, one of the preferred antimetabolites disclosed in European Patent Application No. 239362 such as N-{5-[N-(3,4-dihydro-2-methyl-4-oxoquinazolin-6-ylmethyl)-N-methylamino]2-thenoyl}-L-glutamic acid; intercalating antibiotics, for example adriamycin and bleomycin; enzymes, for example asparaginase; topoisomerase inhibitors, for example etoposide; biological response modifiers, for example interferon; and anti-hormones, for example antioestrogens such as 'NOLVADEX' (tamoxifen) or, for example antiandrogens such as 'CASODEX' (4'-cyano-3-(4-fluorophenylsulphonyl)-2-hydroxy-2-methyl-3'-(trifluoromethyl)propionanilide. Such conjoint treatment may be achieved by way of the simultaneous, sequential or separate dosing of the individual components of the treatment. According to this aspect of the invention there is provided a pharmaceutical product comprising a pyrimidine derivative of the formula I as defined hereinbefore and an additional anti-tumour substance as defined hereinbefore for the conjoint treatment of cancer.

As stated above the pyrimidine derivative defined in the present invention is an effective anti-cancer agent, which property is believed to arise from its Class I receptor tyrosine kinase inhibitory properties. Such a pyrimidine derivative of the invention is expected to possess a wide range of anti-cancer properties as Class I receptor tyrosine kinases have been implicated in many common human cancers such as leukaemia and breast, lung, colon, rectal, stomach, prostate, bladder, pancreas and ovarian cancer. Thus it is expected that a pyrimidine derivative of the invention will possess anti-cancer activity against these cancers. It is in addition expected that a pyrimidine derivative of the present invention will possess activity against a range of leukaemias, lymphoid malignancies and solid tumours such as carcinomas and sarcomas in tissues such as the liver, kidney, prostate and pancreas.

It is further expected that a pyrimidine derivative of the present invention will possess activity against other cell-proliferation diseases such as psoriasis.

The invention will now be illustrated in the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multilicities are shown as follows: s, singlet; d, doublet; t, triplet; m, multiplet;

(vii) intermediates were not generally fully characterised and purity was assessed by thin layer chromatography (TLC), infra-red (IR) or NMR analysis;

(viii) the following abbreviations have been used:
DMF N,N-dimethylformamide;
NMP N-methylpyrrolidin-2-one;
DMSO dimethylsulphoxide.

EXAMPLE 1

A mixture of 6-chloro-4-(3'-chloro-4'-fluoroanilino) pyrimidine (0.2 g) and 4-methoxyaniline (0.15 g) was stirred and heated to 140° C. for 2 hours. The mixture was cooled to ambient temperature. The mixture was triturated under a 4:1 mixture of methylene chloride and methanol. There was thus obtained 4-(3'-chloro-4'-fluoroanilino)-6-(4'-methoxyanilino)pyrimidine (0.11 g, 41%), m.p. 251°–253° C.;

NMR Spectrum: $(CD_3SOCD_3)$ 3.7 (s, 3H), 6.0 (s, 1H), 6.9 (d, 2H), 7.3–7.5 (m, 2H), 7.4 (d, 2H), 8.0 (m, 1H), 8.2 (s, 1H), 9.0 (s, 1H), 9.3 (s, 1H);

Elemental Analysis: Found C, 58.7; H, 3.9; N, 15.8; $C_{17}H_{14}ClFN_4O$ $0.25H_2O$ requires C, 58.4; H, 4.2; N, 16.0%.

The 6-chloro-4-(3'-chloro-4'-fluoroanilino)pyrimidine was obtained as follows:

A mixture of 4,6-dichloropyrimidine (25 g), 3-chloro-4-fluoroaniline (29.5 g), triethylamine (28.3 ml) and ethanol (150 ml) was stirred and heated to reflux for 4 hours. The mixture was evaporated and the residue was dissolved in methylene chloride (300 ml). Water (150 ml) was added and the precipitate was isolated. The solid so obtained was recrystallised from a mixture of ethanol and water. There was thus obtained 6-chloro-4-(3'-chloro-4'-fluoroanilino) pyrimidine (19 g, 44%), m.p. 177°–179° C.;

NMR Spectrum: $(CD_3SOCD_3+CD_3CO_2D)$ 6.81 (s, 1H), 7.34 (t, 1H), 7.5 (m, 1H), 8.0 (m, 1H), 8.5 (s, 1H).

EXAMPLE 2

A mixture of 6-chloro-4-(3'-chloro-4'-fluoroanilino)-pyrimidine (0.5 g), 3-chloroaniline (7 ml), triethylamine (0.27 ml) and NMP (15 ml) was stirred and heated to 145° C. for 18 hours. The mixture was cooled to ambient temperature and partitioned between ethyl acetate and water. The organic phase was washed with water and with brine, dried $(MgSO_4)$ and evaporated. The residue was dissolved in methyiene chloride and hexane was added. The resultant precipitate was purified by column chromatography using a 19:1 mixture of methylene chloride and methanol as eluent. There was thus obtained 6-(3'-chloroanilino)-4-(3'-chloro-4'-fluoroanilino)pyrimidine (0.38 g, 56%), m.p. 228°–230° C.;

NMR Spectrum: $(CD_3SOCD_3)$ 6.1 (d, 1H), 6.99 (m, 1H), 7.3–7.5 (m, 4H), 7.87 (t, 1H), 7.97 (m, 1H), 8.37 (s, 1H), 9.4 (d, 2H);

Elemental Analysis: Found C, 54.7; H, 3.2; N, 15.6; $C_{16}H_{11}Cl_2FN_4$ requires C, 55.0; H, 3.2; N, 16.0%.

EXAMPLE 3

The procedure described in Example 1 was repeated except that the appropriate aniline was used in place of 4-methoxyaniline. There were thus obtained the compounds described below.

Example 3(1): 4-(3'-chloro-4'-fluoroanilino)-6-anilinopyrimidine in 51% yield, m.p. >250° C.;

NMR Spectrum: $(CD_3SOCD_3)$ 6.1 (s, 1H), 7.0 (t, 1H), 7.3 (m, 3H), 7.4 (m, 1H), 7.6 (d, 2H), 8.0 (m, 1H), 8.3 (s, 1H), 9.2 (s, 1H), 9.3 (s, 1H);

Elemental Analysis: Found C, 60.9; H, 3.6; N, 17.5; $C_{16}H_{12}ClFN_4$ requires C, 61.1; H, 3.8; N, 17.8%.

Example 3(2): 4-(3'-chloro-4'-fluoroanilino)-6-(4'-dimethylaminoanilino)pyrimidine in 20% yield, m.p. >250° C.;

NMR Spectrum: $(CD_3SOCD_3)$ 2.9 (s, 6H), 5.9 (s, 1H), 6.8 (d, 2H), 7.2 (d, 2H), 7.3 (d, 1H), 7.4 (m, 1H), 8.0 (m, 1H), 8.2 (s, 1H), 8.7 (s, 1H), 9.1 (s, 1H);

Elemental Analysis: Found C, 60.1; H, 4.7; N, 19.4; $C_{18}H_{17}FClN_5$ requires C, 60.4; H, 4.8; N, 19.6%.

Example 3(3): 4-(3'-chloro-4'-fluoroanilino)-6-[4'-(2-hydroxyethoxy)anilino]pyrimidine in 77% yield, m.p. 180°–184° C.;

NMR Spectrum: $(CD_3SOCD_3)$ 3.7 (t, 2H), 4.0 (t, 2H), 6,.05 (s, 1H), 7.0 (d, 2H), 7.3 (d, 2H), 7.4 (m, 2H), 7.8 (d, 1H), 8.4 (s, 1H), 10.0 (s, 1H), 10.3 (s, 1H);

Elemental Analysis: Found C, 50.0; H, 3.9; N, 12.8; $C_{18}H_{16}ClFN_4O_2$ 1HCl $1H_2O$ requires C, 50.3; H, 4.4; N, 13.0%.

Example 3(4): 4-(3'-chloro-4'-fluoroanilino)-6-[3'-chloro-4'-(2-hydroxyethoxy)anilino]pyrimidine in 18% yield, m.p. 209°–213° C.;

NMR Spectrum: $(CD_3SOCD_3)$ 3.7 (t, 2H), 4.1 (t, 2H), 6.1 (s, 1H), 7.2 (d, 1H), 7.4 (m, 3H), 7.6 (d, 1H), 7.8 (m, 1H), 8.4 (s, 1H), 9.8 (s, 1H), 10.0 (s, 1H);

Elemental Analysis: Found C, 47.5; H, 3.7; N, 11.6; $C_{18}H_{15}Cl_2FN_4O_2$ 1HCl $0.5H_2O$ requires C, 47.5; H, 3.7; N, 12.3%.

The 3-chloro-4-(2-hydroxyethoxy)aniline used as a starting material in the preparation of Example 3(4) was obtained as follows:

Potassium tert-butoxide (1 g) was added portionwise to a stirred mixture of 3-chloro-4-fluoronitrobenzene (3.5 g), ethylene glycol (5 ml) and DMF (10 ml). The mixture was stirred and heated to 60° C. for 4 hours. The mixture was poured into water (100 ml), acidified by the addition of concentrated hydrochloric acid and extracted with ethyl acetate. The organic phase was washed with water, dried $(MgSO_4)$ and evaporated. The residue was recrystallised from a mixture of hexane and ethyl acetate. There was thus obtained 3-chloro-4-(2-hydroxyethoxy)nitrobenzene (1.3 g, 32%).

A mixture of the material so obtained, concentrated hydrochloric acid (10 ml) and stannous chloride (3 g) was stirred and heated to reflux for 3 hours. The mixture was poured into water (100 ml) and extracted with ethyl acetate. The aqueous solution was basified by the addition of a 10N aqueous sodium hydroxide solution and extracted with ethyl acetate. The organic phase was washed with water, dried $(MgSO_4)$ and evaporated. There was thus obtained 3-chloro-4-(2-hydroxyethoxy)aniline (0.6 g, 50%);

NMR Spectrum: $(CD_3SOCD_3)$ 3.66 (t, 2H), 3.87 (t, 2H), 4.74 (t, 1H), 4.87 (s, 2H), 6.44 (m, 1H), 6.6 (d, 1H), 6.8 (d, 1H).

EXAMPLE 4

The procedure described in Example 2 was repeated except that the appropriate aniline was used in place of 3-chloroaniline. There was thus obtained the compounds described below.

Example 4(1): 4-(31-chloro-41-fluoroanilino)-6-(2'-methylanilino)pyrimidine in 38% yield, m.p. 178°–180° C.;

NMR Spectrum: $(CD_3SOCD_3)$ 2.2 (s, 3H), 5.7 (s, IH), 7.09–7.45 (mn, 6H), 7.99 (m, 1H), 8.21 (s, 1H), 8.58 (s, 1H), 9.2 (s, 1H);

Elemental Analysis: Found C, 61.9; H, 4.2; N, 16.9; $C_{17}H_{14}ClFN_4$ requires C, 62.1; H, 4.3; N, 17.0%.

Example 4(2): 4-(3'-chloro-4'-fluoroanilino)-6-(3'-methylanilino)pyrimidine in 72% yield, m.p. 250°–252° C.;

NMR Spectrum: (CD$_3$SOCD$_3$) 2.28 (s, 3H), 6.11 (s, 1H), 6.81 (d, 1H), 7.15–7.48 (m, 5H), 7.98 (s, 1H), 8.3 (s, 18), 9.1 (s, 1H), 9.3 (s, 1H);

Elemental Analysis: Found C, 61.6; H, 4.3; N, 17.0; C$_{17}$H$_{14}$ClFN$_4$ requires C, 62.1; H, 4.3; N, 17.0%.

Example 4(3): 4-(3'-chloro-4'-fluoroanilino)-6-(4'-methylanilino)pyrimidine in 74% yield, m.p. >250° C.;

NMR Spectrum: (CD$_3$SOCD$_3$) 2.25 (s, 3H), 6.18 (s, 1H), 7.11 (d, 2H), 7.3–7.49 (m, 4H), 7.98 (m, 1H), 8.29 (s, 1H), 9.05 (s, 1H), 9.27 (s, 1H);

Elemental Analysis: Found C, 62.4; H, 4.3; N, 16.9; C$_{17}$H$_{14}$ClFN$_4$ requires C, 62.1; H, 4.3; N, 17.0%.

Example 4(4): 6-(4'-chloroanilino)-4-(3'-chloro-4'-fluoroanilino)pyrimidine in 44% yield, m.p. 235°–237° C.;

NMR Spectrum: (CD$_3$SOCD$_3$) 5.95 (s, 1H), 7.1–7.2 (m, 3H), 7.23–7.34 (m, 1H), 7.45 (d, 2H), 7.8 (m, 1H), 8.16 (s, 1H), 9.17 (d, 2H);

Elemental Analysis: Found C, 55.3; H, 3.1; N, 16.0; C$_{16}$H$_{11}$Cl$_2$FN$_4$ requires C, 55.0; H, 3.2; N, 16.0%.

Example 4(5): 4-(3'-chloro-4'-fluoroanilino)-6-(4'-cyanoanilino)pyrimidine in 30% yield, m.p. >250° C.;

NMR Spectrum: (CD$_3$SOCD$_3$) 6.21 (d, 1H), 7.32 (d, 1H), 7.47 (m, 1H), 7.71 (m, 2H), 7.85 (m, 2H), 7.9 (m, 1H), 8.41 (s, 1H), 9.5 (s, 1H), 9.78 (s, 1H);

Elemental Analysis: Found C, 60.5; H, 3.5; N, 20.5; C$_{17}$H$_{11}$ClFN$_5$ requires C, 60.1; H, 3.3; N, 20.6%.

EXAMPLE 5

Using an analogous procedure to that described in Example 2, 6-chloro-4-(3'-methylanilino)pyrimidine was reacted with 3-methylaniline to give 4,6-di-(3'-methylanilino)pyrimidine in 25% yield, m.p. 242°–244° C.;

NMR Spectrum: (CD$_3$SOCD$_3$) 2.28 (s, 6H), 6.14 (s, 1H), 6.78 (d, 2H), 7.16 (t, 2H), 7.32 (d, 4H), 8.22 (s, 1H), 9.0 (s, 2H);

Elemental Analysis: Found C, 73.5; H, 6.2; N, 18.8; C$_{18}$H$_{18}$N$_4$ requires C, 74.5; H, 6.2; N, 19.3%.

The 6-chloro-4-(3'-methylanilino)pyrimidine used as a starting material was obtained by the reaction of 4,6-dichloropyrimidine and 3-methylaniline using an analogous procedure to that described in the portion of Example 1 which is concerned with the preparation of starting materials.

EXAMPLE 6

A mixture of 6-chloro-4-(3'-chloro-4'-fluoroanilino)pyrimidine (0.4 g) and 3,4-dimethoxyaniline (0.54 g) was stirred and heated to 140° C. for 4 hours. The mixture was cooled to ambient temperature and the mixture triturated under methylene chloride to give a black solid. The liquors were chromatographed on a silica column using ethyl acetate as eluent and the product combined with the black solid. There was thus obtained, after recrystallisation from a mixture of ethyl acetate/hexane, 4-(3'-chloro-4'-fluoroanilino)-6-[3',4'-dimethoxyanilino]pyrimidine in 12% yield, m.p. 192°–195° C.;

NMR Spectrum: (CD$_3$SOCD$_3$) 3.3 (s, 6H), 6.0 (s, 1H), 6.9 (d, 1H), 7.0 (m, 1H), 7.3 (t, 1H), 7.4 (m, 1H), 8.0 (m, 1H), 8.25 (s, 1H), 8.9 (s, 1H), 9.25 (s, 1H);

Elemental Analysis: Found C, 56.5; H, 4.4; N, 14.6; C$_{18}$H$_{16}$N$_4$ClO$_2$ 0.5H$_2$O requires C, 56.4; H, 4.1; N, 14.5%.

EXAMPLE 7

Using an analogous reaction procedure to that described in Example 6, 6-chloro-4-(3'-chloro-4'-fluoroanilino)pyrimidine was reacted with 3-methoxyaniline. The reaction product was recrystallised from a mixture of methylene chloride, methanol and hexane, to give 4-(3'-chloro-4'-fluoroanilino)-6-(3'-methoxyanilino)pyrimidine in 16% yield, m.p. 214°–216° C.;

NMR Spectrum: (CD$_3$SOCD$_3$) 3.3 (s, 3H), 6.1 (s, 1H), 6.6 (m, 1H), 7.05–7.25 (m, 3H), 7.35 (d, 1H), 7.45 (m, 1H), 8.0 (m, 1H), 8.3 (s, 1H), 9.2 (s, 1H), 9.34 (s, 1H);

Elemental Analysis: Found C, 59.1; H, 3.6; N, 15.9; C$_{17}$H$_{14}$ClFN$_4$O requires C, 59.2; H, 3.6; N, 15.9%.

EXAMPLE 8

Using an analogous reaction procedure to that described in Example 6, 6-chloro-4-(3'-chloro-4'-fluoroanilino)pyrimidine (0.258 g) was reacted with 4-methoxycarbonylmethoxyaniline (0.195 g). The reaction product was chromatographed on silica and precipitated from a mixture of methylene chloride, methanol and hexane to give 4-(3'-chloro-4'-fluoroanilino)-6-(4'-methoxycarbonylmethoxyanilino)pyrimidine in 26% yield, m.p. 191°–193° C.

NMR Spectrum: (CD$_3$SOCD$_3$) 3.7 (s, 3H), 4.8 (s, 2H), 6.0 (s, 1H), 6.9 (d, 2H), 7.2 (t, 1H), 7.4–7.5 (m, 3H), 8.0 (m, 1H), 8.2 (s, 1H), 8.9 (s, 1H), 9.2 (s, 1H);

Elemental Analysis: Found C, 55.7; H, 3.9; N, 13.4; C$_{19}$H$_{16}$ClFN$_4$O$_3$ 0.5H$_2$O requires C, 55.5; H, 4.1; N, 13.6%.

EXAMPLE 9

The procedure described in Example 8 was repeated except that the appropriate aniline was used in place of 4-methoxycarbonylmethoxyaniline. There were thus obtained the compounds described below.

Example 9(1) 4-[4'-(Carbamoylmethoxy)anilino]6-(3'-chloro-4'-fluoroanilino)pyrimidine in 12% yield;

NMR Spectrum: (CD$_3$SOCD$_3$) 4.4 (s, 2H), 6.0 (s, 1H), 6.9 (d, 2H), 7.3 (t, 1H), 7.4–7.5 (m, 5H), 8.0 (m, 1H), 8.2 (s, 1H), 9.0 (s, 1H), 9.3 (s, 1H);

Elemental Analysis: Found C, 55.5; H, 4.0; N, 16.7; C$_{18}$H$_{15}$ClFN$_5$O$_2$ requires C, 55.8; H, 3.9; N, 18.1%.

Example 9(2) 4-(3'-Chloro-4'-fluoroanilino)-6-[4'-(N,N-dimethylcarbamoylmethoxy)anilino]pyrimidine in 10% yield;

NMR Spectrum: (CD$_3$SOCD$_3$) 2.8 (s, 3H), 3.0 (s, 3H), 4.6 (s, 2H), 6.0 (s, 1H), 6.9 (d, 2H), 7.4 (m, 4H), 8.0 (m, 1H), 8.2 (s, 1H), 8.9 (s, 1H), 9.2 (s, 1H);

Elemental Analysis: Found C, 56,6; H, 4.7; N, 14.9; C$_{20}$H$_{19}$ClFN$_5$O$_2$ requires C, 57.8; H, 4.6; N, 16.8%.

EXAMPLE 10

Using an analogous reaction procedure to that described in Example 6, 6-chloro-4-(3'-chloro-4'-fluoroanilino)pyrimidine (0.4 g) was reacted with 3-(N,N-dimethylamino)aniline (2 ml). The reaction product was chromatographed on silica and recrystallised from a mixture of methylene chloride and hexane to give 4-(3'-chloro-4'-fluoroanilino)-6-[3'-(N,N-dimethylamino)anilino]pyrimidine in 10% yield, m.p. 207°–210° C.;

NMR Spectrum: (CD$_3$SOCD$_3$) 2.9 (s, 6H), 6.1 (s, 1H), 6.4 (m, 1H), 6.8 (m, 2H), 7.1 (t, 1H), 7.3 (t, 1H), 7.45 (m, 1H), 8.0 (m, 1H), 8.3 (s, 1H), 9.0 (s, 1H), 9.3 (s, 1H);

Elemental Analysis: Found C, 59.9; H, 4.6; N, 19.3; C$_{18}$H$_{17}$ClFN$_5$ requires C, 60.4; H, 4.8; N, 19.6%.

EXAMPLE 11

Using an analogous reaction procedure to that described in Example 6, 6-chloro-4-(3'-chloro-4'-fluoroanilino)

pyrimidine (0.258 g) was reacted with 4-(2-methoxyethoxy) aniline (0.206 g). The reaction product was chromatographed on silica and precipitated from a mixture of methylene chloride and hexane to give 4-(3'-chloro-4'-fluoroanilino)-6-[4'-(2-methoxyethoxy)anilino]pyrimidine in 49% yield, m.p. 208°–210° C.;

NMR Spectrum: (CD$_3$SOCD$_3$) 3.3 (s, 3H), 3.65 (t, 2H), 4.1 (t, 2H), 6.0 (s, 1H), 6.9 (d, 2H), 7.3 (t, 1H), 7.4–7.5 (m, 3H), 8.0 (m, 1H), 8.3 (s, 1H), 8.9 (s, 1H), 9.2 (s, 1H);

Elemental Analysis: Found C, 56.4; H, 4.3; N, 13.9; C$_{19}$H$_{19}$ClFN$_4$O$_2$ requires C, 58.7; H, 4.7; N, 14.4%.

The 4-(2-methoxyethoxy)aniline used as starting material was obtained as follows:

Potassium tert-butoxide (2 g) was added portionwise to a stirred mixture of 4-fluoronitrobenzene (2.8 g), 2-methoxyethanol (10 ml) and DMF (20 ml). The mixture was stirred and heated to 60° C. for 4 hours. The mixture was diluted with water and extracted with ethyl acetate. The organic phase was washed with water and with brine, dried (MgSO$_4$)- and evaporated. The residue was recrystallised from a mixture of hexane and ethyl acetate. There was thus obtained 4-(2-methoxyethoxy)nitrobenzene (1.06 g), m.p. 86° C.

The product so obtained was dissolved in ethyl acetate and hydrogenated in the presence of a 10% Pd/C catalyst to give 4-(2-methoxyethoxy)aniline (0.7 g).

NMR Spectrum: (CD$_3$SOCD$_3$) 3.3 (s, 3H), 3.6 (t, 2H), 3.9 (t, 2H), 4.6 (s, 2H), 6.5 (d, 2H), 6.7 (d, 2H).

EXAMPLE 12

Using an analogous reaction procedure to that described in Example 6, 6-chloro-4-(3'-chloro-4'-fluoroanilino) pyrimidine (0.8 g) was reacted with 4-(N-methylcarbamoylmethoxy)aniline (0.56 g). The reaction product was chromatographed on silica and recrystallised from a mixture of ethyl acetate and hexane to give 4-(3'-chloro-4'-fluoroanilino)-6-[4'-(N-methylcarbamoylmethoxy)anilino]pyrimidine in 9% yield, m.p. 213°–216° C.;

NMR Spectrum: (CD$_3$SOCD$_3$) 2.7 (d, 3H), 4.4 (s, 2H), 6.0 (s, 1H), 6.9 (d, 2H), 7.3 (t, 1H), 7.4 (m, 3H), 8.0 (m, 2H), 8.25 (s, 1H), 9.0 (s, 1H), 9.3 (s, 1H);

Elemental Analysis: Found C, 56.6; H, 4.2; N, 17.2; C$_{19}$H$_{17}$ClFN$_5$O$_2$ requires C, 56.8; H, 4.3; N, 17.4%.

The 4-(N-methylcarbamoylmethoxy)aniline used as starting material was obtained as follows:

A mixture of ethyl 4-nitrophenoxyacetate (2 g) and 33% methylamine in ethanol was refluxed for 2 hours to give 4-(N-methylcarbamoylmethoxy)nitrobenzene (1.57 g);

NMR Spectrum: (CD$_3$SOCD$_3$) 2.6 (d, 3H), 4.6 (s, 2H), 7.2 (d, 2H), 8.1 (s, 1H), 8.2 (d, 2H).

The product so obtained was dissolved in ethyl acetate and hydrogenated in the presence of a 10% Pd/C catalyst to give 4-(N-methylcarbamoylmethoxy)aniline (0.72 g);

NMR Spectrum: (CD$_3$SOCD$_3$) 2.6 (d, 3H), 4.3 (s, 2H), 4.6 (s, 2H), 6.5 (d, 2H), 6.7 (d, 2H), 6.9 (s, 1H).

EXAMPLE 13

Using an analogous reaction procedure to that described in Example 6, 4-chloro-6-[4'-(2-hydroxyethoxy)anilino] pyrimidine (0.52 g) (prepared from the reaction of 4,6-dichloropyrimidine and 4-(2-hydroxyethoxy)aniline) was reacted with 2-fluoroaniline (1 ml). The reaction product was chromatographed on silica and recrystallised from a mixture of methylene chloride, methanol and hexane to give 4-(2'-fluoroanilino)- 6-[4'-(2-hydroxyethoxy)anilino]pyrimidine in 24% yield, m.p. 163°–166° C.;

NMR Spectrum: (CD$_3$SOCD$_3$) 3.7 (t, 2H), 4.0 (t, 2H), 6.0 (s, 1H), 6.9 (d, 2H), 7.2 (m, 3H), 7.4 (m, 2H), 7.6 (m, 1H), 8.2 (s, 1H), 9.0 (s, 1H), 9.2 (s, 1H);

Elemental Analysis: Found C, 61.2; H, 5.0; N, 15.8; C$_{18}$H$_{17}$FN$_4$O$_2$ requires C, 63.5; H, 5.0; N, 16.5%.

EXAMPLE 14

A mixture of 6-chloro-4-[4'-(2-hydroxyethoxy)anilino] pyrimidine (1.0 g), 3-methylaniline (5 ml) and NMP (20 ml) was stirred and heated to 140° C. for 72 hours. The mixture was cooled and partitioned between ethyl acetate and water. The precipitate was removed by filtration, the ethyl acetate fraction chromatographed on silica and the combined products extracted with boiling ethyl acetate. The product was recrystallised from a mixture of ethyl acetate and hexane to give 4-[4'-(2-hydroxyethoxy)anilino]6-(3'-methylanilino) pyrimidine in 20% yield, m.p. 196°–199° C.;

NMR Spectrum: (CD$_3$SOCD$_3$) 2.3 (s, 3H), 3.7 (m, 2H), 4.0 (t, 2H), 4.8 (t, 1H), 6.0 (s, 1H), 6.65 (d, 1H), 6.7 (d, 2H), 7.1 (t, 1H), 7.25–7.45 (m, 4H), 8.2 (s, 1H), 8.8 (s, 1H), 9.0 (s, 1H);

Elemental Analysis: Found C, 66.1; H, 6.1; N, 16.2; C$_{19}$H$_{20}$N$_4$O$_2$ 0.5H$_2$O requires C, 66.3; H, 5.9; N, 16.1%.

EXAMPLE 15

Using an analogous reaction procedure to that described in Example 6, 4-chloro-6-(3'-methylanilino)pyrimidine (1.0 g) was reacted with 4-cyanomethoxyaniline (0.6 g). The reaction product was chromatographed on silica to give 4-(4'-cyanomethoxyanilino)-6-(3'-methylanilino)pyrimidine in 24% yield, m.p. 207°–210° C.;

NMR Spectrum: (CD$_3$SOCD$_3$) 2.2 (s, 3H), 5.1 (s, 2H), 6.1 (s, 1H), 6.8 (d, 1H), 7.0 (d, 2H), 7.1 (d, 2H), 7.15 (t, 1H), 7.45 (d, 2H), 8.2 (s, 1H), 9.0 (s, 1H);

Elemental Analysis: Found C, 68.6; H, 5.1; N, 20.8; C$_{19}$H$_{17}$N$_5$O requires C, 68.9; H, 5.2; N, 21.1%.

EXAMPLE 16

Using an analogous reaction procedure to that described in Example 6, 6-chloro-4-(3$^1$-methylanilino)pyrimidine (0.435 g) was reacted with 4-(N-methylcarbamoylmethoxy) aniline (0.380 g) to give 4-(3'-methylanilino)-6-[4'-(N-methylcarbamoylmethoxy)anilino]pyrimidine in 15% yield, m.p. 135°–138° C.;

NMR Spectrum: (CD$_3$SOCD$_3$) 2.3 (s, 3H), 2.65 (d, 3H), 4.5 (s, 2H), 6.0 (s, 1H), 7.0 (m, 3H), 7.3–7.4 (m, 5H), 8.0 (d, 1H), 8.4 (s, 1H), 10.05 (s, 1H), 10.1 (s, 1H);

Elemental Analysis: Found C, 60.2; H, 5.7; N, 17.0; C$_{20}$H$_{20}$N$_5$O$_2$ HCl requires C, 60.2; H, 5.5; N, 17.5%.

EXAMPLE 17

Using an analogous reaction procedure to that described in Example 6, 4-chloro-6-(3'-methylanilino)pyrimidine (0.220 g) was reacted with 3-chloro-4-(2-hydroxyethoxy) aniline (0.190 g). The product was chromatographed on silica and recrystallised from a mixture of methylene chloride and hexane to give 4-[3'-chloro-4'-(2-hydroxyethoxy) anilino]6-(3'-methylanilino)pyrimidiie in 23% yield, m.p. 174°–176° C.;

NMR Spectrum: (CD$_3$SOCD$_3$) 2.3 (s, 3H), 3.5 (t, 2H), 4.0 (t, 2H), 4.8 (s, 1H), 6.1 (s, 1H), 7.1 (m, 2H), 7.4 (m, 3H), 7.7 (d, 1H), 8.2 (s, 1H), 9.0 (d, 2H);

Elemental Analysis: Found C, 60.3; H, 5.1; N, 14.8; $C_{19}H_{19}ClN_4O_2$ requires C, 61.5; H, 5.2; N, 15.1%.

EXAMPLE 18

Using an analogous reaction procedure to that described in Example 6, 6-chloro-4-(3'-methylanilino)pyrimidine (0.410 g) was reacted with 4-(N,N-dimethylcarbamoylmethoxy)aniline (0.420 g). The product was chromatographed on silica and recrystallised from a mixture of methylene chloride and hexane to give 4-(3'-methylanilino)-6-[4'-(N,N-dimethylcarbamoylmethoxy)anilino]pyrimidine in 15% yield, m.p. 135°–138° C.;

NMR Spectrum: $(CD_3SOCD_3)$ 2.2 (s, 3H), 2.65 (s, 3H), 3.0 (s, 3H), 4.6 (s, 2H), 6.0 (s, 1H), 6.6 (d, 1H), 6.65 (d, 2H), 7.15 (t, 1H), 7.35 (m, 4H), 8.2 (s, 1H), 8.8 (s, 1H), 9.0 (s, 1H);

Elemental Analysis: Found C, 66.1; H. 6.2; N, 18.1; $C_{21}H_{23}N_5O_2$ requires C, 66.8; H, 6.1; N, 18.6%.

The 4-(N,N-dimethylcarbamoylmethoxy)aniline used as starting material was obtained by the reaction of ethyl 4-nitrophenoxyacetate and 33% dimethylamine in ethanol, followed by hydrogenation, using an analogous procedure to that described in the portion of Example 12 which is concerned with the preparation of starting materials;

NMR Spectrum: $(CD_3SOCD_3)$ 2.6 (s, 3H), 3.0 (s, 3H), 4.56 (s, 2H), 4.7 (s, 2H), 6.46–6.66 (m, 4H).

EXAMPLE 19

Using an analogous procedure to that described in Example 18, 4-chloro-6-(3'-methylanilino)pyrimidine (0.33 g) was reacted with 3-chloro-4-(N,N-dimethylcarbamoylmethoxy)aniline to give 4-[3'-chloro-4'-(N,N-dimethylcarbamoylmethoxy)anilino]-6-(3'-methylanilino)pyrimidine is 46% yield, m.p. 190°–193° C.;

NMR Spectrum: $(CD_3SOCD_3)$ 2.3 (s, 3H), 2.8 (s, 3H), 3.0 (s, 3H), 4.86 (s, 2H), 6.1 (s, 1H), 6.6 (d, 1H), 7.0 (d, 1H), 7.2, t, 1H), 7.3 (m, 2H), 7.7 (d, 1H), 8.2 (s, 1H), 9.0 (s, 2H);

Elemental Analysis: Found C, 61.3; H, 5.7; N, 16.2; $C_{21}H_{22}ClN_5O_2$ requires C, 61.2; H, 5.3; N, 17.0%.

The 3-chloro-4-(N,N-dimethylcarbamoylmethoxy)aniline used as starting material was obtained as follows:

A mixture of 2-chloro-4-nitrophenol (1.74 g), methyl bromoacetate (1.1 ml) and potassium carbonate (1.6 g) in DMF (10 ml) was stirred at ambient temperature to give methyl 2-chloro-4-nitro-phenoxy acetate (2.4 g). The product so obtained was reacted with 30% dimethylamine in ethanol, followed by hydrogenation in the presence of a 5% Pt/C catalyst. The product so obtained was recrystallised from a mixture of ethyl acetate and hexane to give 3-chloro-4-(N,N-dimethylcarbamoylmethoxy)aniline;

NMR Spectrum: $(CD_3SOCD_3)$ 2.8 (s, 3H), 3.0 (s, 3H), 4.6 (s, 2H), 4.9 (s, 2H), 6.4 (m, 1H), 6.6 (d, 1H), 6.8 (d, 1H).

EXAMPLE 20

Using an analogous procedure to that described in Example 13, 4-chloro-6-(3'-methylanilino)pyrimidine (0.23 g) was reacted with 4-(carbamoylmethoxy)aniline to give 4-[4'-(carbamoylmethoxy)anilino]6-(3'-methylanilino) pyrimidine in 30% yield, m.p. 212°–215° C.;

NMR Spectrum: $(CD_3SOCD_3)$ 2.25 (s, 3H), 4.4 (s, 2H), 6.0 (s, 1H), 6.8 (d, 1H), 6.9 (d, 2H), 7.1 (t, 1H), 7.4 (m, 6H), 8.2-(s, 1H), 8.8 (s, 1H), 9.0 (s, 1H);

Elemental Analysis: Found C, 62.6; H, 5.7; N, 19.0; $C_{19}H_{19}N_5O_2$ requires C, 65.3; H, 5.5; N, 20.0%.

The 4-(carbamoylmethoxy)aniline used as starting material was obtained as follows:

A mixture of 4-nitrophenol (2.8 g), iodoacetamide (3.72 g) and potassium carbonate (2.8 g) in DHF (50 ml) was reacted. The product so obtained was recrystallised from a mixture of ethyl acetate and hexane to give 4-(carbamoylmethoxy)nitrobenzene (1.32 g), m.p. 153°–156° C. The product so obtained was dissolved in ethyl acetate and hydrogenated in the presence of a 10% Pd/C catalyst. The product so obtained was recrystallised from a mixture of ethyl acetate and hexane to give 4-(carbamoylmethoxy)aniline (0.58 g), m.p. 125°–127° C.;

NMR Spectrum: $(CD_3SOCD_3)$ 4.3 (s, 2H), 4.6 (s, 2H), 6.45–6.75 (m, 4H), 7.3 (s, 1H).

EXAMPLE 21

Using an analogous reaction procedure to that described in Example 6, 4-chloro-6-(3'-methylanilino)pyrimidine (1.35 g) was reacted with 4-(3-hydroxypropoxy)aniline.(1.0 g). The product so obtained was chromatographed on silica and triturated under methylene chloride to give 4-[4'-(3-hydrox-ypropoxy)anilino]6-(3'-methylanilino)pyrimidine in 18% yield, m.p. 196°–200° C.;

NMR Spectrum: $(CD_3SOCD_3)$ 1.85 (m, 2H), 2.3 (s, 3H), 3.6 (m, 2H), 4.0 (t, 2H), 4.5 (t, 1H), 6.0 (s, 1H), 6.8 (d, 1H), 6.9 (d, 2H), 7.1 (t, 1H), 7.3 (m, 4H), 8.1 (s, 1H), 8.8 (s, 1H), 8.9 (s, 1H);

Elemental Analysis: Found C, 58.6; H, 6.1; N, 13.6; $C_{20}H_{22}N_4O_2$ requires C, 68.6; H, 6.3; N, 16.0%.

The 4-(3-hydroxypropoxy)aniline used as starting material was prepared from 4-fluoronitrobenzene and 1,3-propanediol using an analogous procedure to that described in the section of Example 3(4) which relates to the preparation of starting materials.

EXAMPLE 22

Using an analogous reaction procedure to that described in Example 6, 6-chloro-4-(4'-hydroxyanilino)pyrimidine (3.2 g) was reacted with 3-methylaniline (5 ml). The product so obtained was triturated under methylene chloride. The solid so obtained was filtered off and extracted with hot water. On cooling a solid precipitated from the aqueous solution. The solid was extracted from the aqueous solution with ethyl acetate, washed with water and with brine, dried $(MgSO_4)$ and recrystallised from a mixture of ethyl acetate and hexane to give 4-(4'-hydroxyanilino)-6-(3'-methylanilino)pyrimidine (0.15 g), m.p. 242°–245° C.;

NMR Spectrum: $(CD_3SOCD_3)$ 2.3 (s, 3H), 6.0 (s, 1H), 6.65–6.8 (m, 3H), 7.1–7.2 (m, 3H), 7.3–7.4 (d, 2H), 8.1 (s, 1H), 8.6 (s, 1H), 8.6 (s, 1H), 8.9 (s, 1H);

Elemental Analysis: Found C, 69.5; H, 6.3; N. 16.8; $C_{17}H_{16}N_4O$ requires C, 69.8; H, 5.5; N, 19.2%.

The 6-chloro-4-(4'-hydroxyanilino)pyrimidine used as starting material was obtained as follows:

A mixture of 4,6-dichloropyrimidine (3.0 g), 4-aminophenol (2.2 g) and triethylamine (6 ml) in ethanol. (50 ml) was refluxed for 2 hours. The product so obtained was recrystallised from a mixture of ethyl acetate and hexane to give 6-chloro-4-(4'-hydroxyanilino)pyrimidine in 76% yield, m.p. 241–244° C.;

NMR Spectrum: $(CD_3SOCD_3)$ 6.6 (s, 1H), 6.75 (d, 2H), 7.25 (d, 2H), 8.3 (s, 1H), 9.3 (s, 1H), 9.6 (s, 1H).

EXAMPLE 23

A solution of 4-(4'-hydroxyanilino)-6-(3'-methylanilino) pyrimidine (0.6 g) in toluene (5 ml) and DMF (10 ml) was added to a stirred suspension of sodium hydride (0.1 g, 60%) in toluene (20 ml). After effervescence stopped the reaction mixture was brought to reflux. A solution of 2-dimethylaminoethyl chloride free base in toluene (50 ml) was obtained by neutralization of the hydrochloride salt (1.6 g) and extraction into toluene, and was added to the reaction mixture. The reaction mixture was refluxed for 3 hours. The product so obtained was partitioned with water, the organic phase extracted, evaporated and the residue recrystallised from a mixture of methylene chloride, methanol and hexane to give 4-[4'-(2-dimethylaminoethoxy)anilino]6-(3'-methylanilino)pyrimidine in 48% yield, m.p. 219°–222° C.;

NMR Spectrum: (CD$_3$SOCD$_3$) 2.2 (s, 6H), 2.3 (s, 3H), 2.6 (t, 2H) 4.0 (t, 2H), 6.0 (s, 1H), 6.75 (d, 1H), 6.9 (d, 2H), 7.15 (t, 1H), 7.3–7.4 (m, 4H), 8.2 (s, 1H), 8.85 (s, 1H), 8.95 (s, 1H);

Elemental Analysis: Found C, 65.8; H, 6.5; N, 18.2; C$_{21}$H$_{25}$N$_5$O 1H$_2$O requires C, 66.1; H, 7.1; N, 18.4%.

EXAMPLE 24

Using an analogous reaction procedure to that described in Example 23, 4-(4'-hydroxyanilino)-6-(3'-methylanilino) pyrimidine (0.6 g) was reacted with 3-dimethylaminopropyl chloride. The product so obtained was chromatographed on silica and precipitated from a mixture of methylene chloride, methanol and hexane to give 4-[4'-(3-dimethylaminopropoxy)anilino]6-(3'-methylanilino) pyrimidine in 13% yield, m.p. 204°–207° C.;

NMR Spectrum: (CD$_3$SOCD$_3$) 1.6 (m, 2H), 2.15 (s, 6H), 2.35 (t, 2H), 4.0 (t, 2H), 6.0 (s, 1H), 6.6 (d, 1H), 6.7 (d, 2H), 7.15 (t, 1H), 7.35 (m, 4H), 8.2 (s, 1H), 8.8 (s, 1H), 8.95 (s, 1H);

Elemental Analysis: Found C, 67.5; H, 7.0; N, 17.7; C$_{22}$H$_{27}$N$_5$O 0.75H$_2$O requires C, 67.6; H, 7.3; N, 17.9%.

EXAMPLE 25

6-(3'-Methylanilino)-4-[3'-(ethoxycarbonylmethoxy) anilino]pyrimidine (0.05 g) was dissolved in 30% methylamine in ethanol (10 ml) and stirred at room temperature for 20 hours. The volatiles were evaporated and the product triturated under diethyl ether to give 6-(3'-methylanilino)-4-[3'-(N-methylcarbamoylmethoxy)anilino]pyrimidine in 79% yield, m.p. 201°–203° C.;

NMR Spectrum: (CD$_3$SOCD$_3$) 2.30 (s, 3H), 2.68 (d, 3H), 4.42 (s, 2H), 6.19 (s, 1H), 6.56 (d, 1H), 6.80 (d, 1H), 7.05–7.4 (m, 6H), 8.0 (d, 1H), 8.27 (s, 1H), 9.03 (s, 1H), 9.12 (s, 1H);

Elemental Analysis: Found C, 64.3; H, 5.9; N, 18.8; C$_{20}$H$_{21}$N$_5$O$_2$ 0.5H$_2$O requires C, 64.3; H, 5.9; N, 18.8%.

The 6-(3'-methylanilino)-4-[3'-(ethoxycarbonylmethoxy) anilino]pyrimidine used as starting material was prepared as follows:

A mixture of 3-nitrophenol (6.95 g), ethyl bromoacetate (8.35 g) and potassium carbonate (6.9 g) in dry NHP (50 ml) was stirred at room temperature for 48 hours. The reaction mixture was partitioned between water (300 ml) and diethyl ether (75 ml). The organic layer was separated, washed with water, brine and dried (MgSO$_4$). The residue was filtered through silica and eluted with a 3:2 mixture of hexane and ethyl acetate to give ethyl 3-nitrophenoxyacetate as a viscous oil in 98% yield;

NMR Spectrum: (CD$_3$SOCD$_3$) 1.22 (t, 3H), 4.19 (m, 2H), 4.98 (s, 2H), 7.22 (t, 1H), 7.44 (m, 1H), 7.60 (t, 1H), 7.86 (m, 1H);

A mixture of ethyl 3-nitrophenoxyacetate (10 g) in ethanol (200 ml), iron powder (10 g) and concentrated hydrochloric acid (4.8 ml) was heated at reflux for 5 hours. The solid residue was removed by filtration whilst the mixture was hot, and was washed with warm ethanol. The solvent was evaporated and the residue partitioned between sodium bicarbonate solution and methylene chloride. The aqueous layer was separated and extracted with fresh methylene chloride. The combined organic extracts were dried (MgSO$_4$) and evaporated. The residue was eluted through silica using a 5:3 mixture of hexane and ethyl acetate as eluent to give ethyl 3-aminophenoxyacetate as an orange oil in 66% yield;

NMR Spectrum: (CD$_3$SOCD$_3$) 1.21 (t, 3H), 4.16 (m, 2H), 4.60 (s, 21H), 5.04 (s, 2H), 6.03 (d, 1H), 6.10 (t, 1)H, 6.18 (m, 1H), 6.89 (t, 1).

Using an analogous procedure to that described in Example 6 ethyl 3-aminophenoxyacetate was reacted with 4-chloro-6-(3-methylanilino)pyrimidine. The product so obtained was chromatographed on silica using a mixture of hexane and ethyl acetate, increasing in polarity from a 2:1 mixture to a 3:2 mixture, as eluent. The product so obtained was triturated with diethyl ether to give 6-(3'-methylanilino) -4-[3-(ethoxycarbonylgethoxy)anilino]pyrimidine in 16% yield, m.p. 162°–164° C., NMR Spectrum: (CD$_3$SOCD$_3$) 1.22 (t, 3H), 2.30 (s, 3H), 4.19 (mn, 2H), 4.72 (s, 2H), 6.19 (m, 1H), 6.52 (d, 1H), 6.81 (d, 1H), 7.05–7.40 (m, 6H), 8.28 (s, 1H), 9.05 (s, 1H), 9.12 (s, 1H).

EXAMPLE 26

Using an analogous procedure to that described in Example 25, 6-(3'-methylanilino)-4-[3'-(ethoxycarbonylmethoxy)anilino]pyrimidine was reacted with saturated methanolic ammonia to give 4-[3'-(carbamoylmethoxy)anilino]6-(3'-methylanilino)pyrimidine in 81% yield, m.p. 192°–194° C.;

NMR Spectrum: (CD$_3$SOCD$_3$) 2.19 (s, 3H), 4.39 (s, 2H), 6.19 (s, 1H), 6.56 (m, 1H), 6.80 (d, 1H), 7.1–7.4 (m 7H), 7.47 (d, 1H), 8.26 (s, 1H), 9.01 (s, 1H), 9.10 (s, 1H);

Elemental Analysis: Found C, 63.3; H, 5.6; N, 19.0; C$_{19}$H$_{19}$N$_5$O$_2$0.5H$_2$ requires C, 63.6; H, 5.5; N, 19.6%.

EXAMPLE 27

Using an analogous reaction procedure to that described in Example 23, 4-(3 '-hydrbxyanilino) -6-(3 '-methylanilino) pyriinidine was reacted with 2-dimethylaminoethyl chloride. The product so obtained was partitioned with water, extracted with ethyl acetate, washed with water and with brine, dried (MgSO$_4$) and evaporated. The residue was dissolved in methylene chloride and chromatographed on silica using a mixture of methylene chloride and methanol, increasing in polarity from pure methylene chloride to a 4:1 mixture of methylene chloride and methanol as eluent. There was thus obtained 4-[3'-(2-dimethylaminoethoxy)anilino]6-(3'-methylanilino)pyrimidine in 6% yield, m.p. 142°–144° C.;

NMR Spectrum: (CD$_3$SOCD$_3$) 2.28 (s, 9H), 2.7 (t, 2H), 4.04 (t, 2H), 6.18 (s, 1H), 6.55 (m, 1H), 6.8 (d, 1H), 7.08 (m, 1H), 7.18 (m, 2H), 7.26–7.38 (m, 3H), 8.27 (s, 1H), 9.04 (s, 1H), 9.08 (s, 1H);

Elemental Analysis: Found C, 63.1; H, 6.5; N, 17.6; C$_{21}$H$_{25}$N$_5$O 1HCl requires C, 63.1; H, 6.5; 17.5%.

The 4-(3'-hydroxyanilino)-6-(3'-methylanilino) pyrimidine used as starting material was obtained as follows:

A mixture of 4-chloro-6-(3'-methylanilino)pyrimidine (9.56 g) and 3-aminophenol (5.22 g) was stirred and heated at 140° C. for 3 hours. The product so obtained was dissolved in methylene chloride and a few drops of methanol, and chromatographed on silica using a mixture of methylene chloride and methanol, increasing in polarity from pure methylene chloride to a 19:1 mixture of methylene chloride and methanol as eluent. The product so obtained was recrystallised from a mixture of ethyl acetate and hexane to give 4-(3'-hydroxyanilino)-6-(3'-methylanilino)pyrimidine in 39% yield, m.p. 188°–189° C.;

NMR Spectrum: ($CD_3SOCD_3$) 2.28 (s, 3H), 6.17 (s, 1H), 6.48 (m, 1H), 6.78 (d, 1H), 6.92 (d, 1H), 7.00–7.22 (m, 3M), 7.30 (d, 1H), 7.33 (s, 1H), 8.22 (s, 1H), 8.95 (d, 2H), 9.28 (s, 1H).

EXAMPLE 28

Using an analogous procedure to that described in Example 27, 4-(3'-hydroxyanilino)-6-(3'-methylanilino) pyrimidine (0.5 g) was reacted with 3-dimethylaminopropyl chloride to give 4-[3'-(3-dimethylaminopropoxy)anilino]-6-(3'-methylanilino)pyrimidine in 16% yield, m.p. 142°–144° C.;

NMR Spectrum: ($CD_3SOCD_3$) 1.85 (t, 2H), 2.2 (s, 6H), 2.3 (s, 3H), 2.41 (t, 2H), 3.98 (t, 2H), 6.18 (s, 1H), 6.54 (m, 1H), 6.8 (d, 1H), 7.03–7.25 (m, 4H), 7.32 (d, 1H), 7.34 (s, 1H), 8.26 (s, 1H), 9.03 (s, 11), 9.06 (s, 1H);

Elemental Analysis: Found C, 60.0; H, 6.5; N, 16.2; $C_{22}H_{27}N_5O$ 1HCl 1.2$H_2O$ requires C, 60.6; H, 7.04; N, 16.8%.

EXAMPLE 29

Using an analogous reaction procedure to that described in Example 6, 6-chloro-4-(3'-chloro-4'-fluoroanilino)pyrimidine (0.52 g) was reacted with 4-[N-(2-hydroxyethyl)carbamoylmethoxy]aniline (0.42 g). The product so obtained was chromatographed on silica and recrystallised from a mixture of ethyl acetate and hexane to give 4-(3'-chloro-4'-fluoroanilino)-6-[4'-{N-(2-hydroxyethyl)carbamoylmethoxy}anilino]pyrimidine in 15% yield, m.p. 203°–206° C.;

NMR Spectrum: ($CD_3SOCD_3+CD_3COOD$) 3.2-(m, 2H), 3.45 (t, 2H), 4.4 (s, 2H), 6.0 (s, 1H), 6.9 (d, 2H), 7.2 (t, 1H), 7.4 (m, 3H), 7.9 (m, 1H), 8.2 (s, 1H);

Elemental Analysis: Found C, 54.9; H, 4.4; N, 15.5; $C_{20}H_{19}ClFN_5O_3$0.5$H_2O$ requires C, 54.5; H, 4.5; N, 15.9%.

The 4-[N-(2-hydroxyethyl)carbamoylmethoxy]aniline used as starting material was obtained as follows:

A mixture of ethyl 4-nitrophenoxyacetate (2.0 g) and 2-aminoethanol (10 ml) in ethanol was reacted at reflux. The product so obtained crystallised on cooling, was dissolved in ethyl acetate and hydrogenated in the presence of a 10% Pd/C catalyst to give 4-[N-(2-hydroxyethyl)carbamoylmethoxy]aniline (1.0 g);

NMR Spectrum: ($CD_3SOCD_3$) 3.2 (m, 2H), 3.45 (m, 2H), 4.25 (s, 2H), 4.7, (m, 3H), 6.4–6.7 (m, 4H), 7.6 (t, 1H).

EXAMPLE 30

Using an analogous reaction procedure to that described in Example 6, 4-chloro-6-(3'-methylanilino)pyrimidine (0.56 g) was reacted with 4-[N-(2-hydroxyethyl)carbamoylmethoxy]aniline (0.54 g). The product so obtained was chromatographed on silica to give 4-[4'-{N-(2-hydroxyethyl)carbamoylmethoxy}anilino]6-(3'-methylanilino)pyrimidine in 8% yield, m.p. 192°–194° C.;

NMR Spectrum: ($CD_3SOCD_3+CD_3COOD$) 2.3 (s, 3H), 3.2 (m, 2H), 3.5 (t, 2H), 4.5 (s, 2H), 6.0 (s, 1H), 6.9 (m, 1H), 7.0 (d, 2H), 7.2 (m, 3H), 7.4 (d, 2H), 8.3 (s, 1H);

Elemental Analysis: Found C, 62.0; H, 5.9; N, 17.0; $C_{21}H_{23}N_5O_3$0.66$H_2O$ requires C, 62.2; H, 6.0; N, 17.3%.

EXAMPLE 31

A mixture of 2-(N,N-dimethylamino)ethylamine (1 ml) in ethanol (10 ml) and 4-[4'-(ethoxycarbonylmethoxy)anilino]6-(3'-methylanilino)pyrimidine (0.20 g) was stirred at reflux for 6 hours, to give, on cooling, 4-[4'-{N-(2-dimethylaminoethyl)carbamoylmethoxy}anilino]6-(3'-methylanilino)pyrimidine in 41% yield, m.p. 177°–180° C.;

NMR Spectrum: ($CD_3SOCD_3$) 2.16 (s, 6H), 2.3 (s, 3H), 2.35 (t, 2H), 3.2 (t, 2H), 4.4 (s, 2H), 6.0(s, 1H), 6.75 (d, 1H), 6.9 (d, 2H), 7.1 (t, 1H), 7.3 (d, 2H), 7.4 (d, 2H), 7.9 (t, 1H), 8.2 (s, 1H), 8.85 (s, 1H), 8.95 (s, 1H);

Elemental Analysis: Found C, 64.3; H, 6.8; N, 19.6; $C_{23}H_{28}N_6O_2$0.5$H_2O$ requires C, 64.3; H, 6.8; N, 19.5%.

The 4-[4'-(ethoxycarbonylmethoxy)anilino]6-(3'-methylanilino)pyrimidine used as starting material was obtained as follows:

Using an analogous reaction procedure to that described in Example 6, 4-chloro-6-(3'-methylanilino)pyrimidine (1.0 g) was reacted with ethyl 4-aminophenoxyacetate (1.0 g). The product so obtained was chromatographed on silica to give 4-[4'-(ethoxycarbonylmethoxy)anilino]6-(3'-methylanilino)pyrimidine (0.57 g).

EXAMPLE 32

A mixture of 4-[4'-(ethoxycarbonylmethoxy)anilino]6-(3'-methylanilino)pyrimidine (0.30 g) and diethanolamine (0.5 g) in ethanol (10 ml) was refluxed for 8 hours. The product so obtained was chromatographed on silica to give 4-[4'-{N,N-di-(2-hydroxyethyl)carbamoylmethoxy}anilino]6-(3'-methylanilino)pyrimidine in 21% yield, m.p. 160°–162° C.;

NMR Spectrum: ($CD_3SOCD_3$) 2.3 (s, 3H), 3.3–3.6 (m, 8H), 4.6 (t, 1H), 4.8 (s, 2H), 5.0 (t, 1H), 6.0 (s, 1H), 6.7 (d, 1H), 6.8 (d, 2H), 7.1 (t, 1H), 7.3 (m, 4H), 8.2 (s, 1H), 8.8 (s, 1H), 9.0 (s, 1H);

Elemental Analysis: Found C, 60.9; H, 6.4; N, 14.7; $C_{23}H_{27}N_5O_4$1$H_2O$ requires C, 60.7; H, 6.4; N, 15.4%.

EXAMPLE 33

A mixture of 4-[4'-(2,3-epoxypropoxy)anilino]6-(3'-methylanilino) pyrimidine (0.35 g), 33% dimethylamine in ethanol (10 ml) and DMF (5 ml) was stirred at room temperature for 4 hours. The mixture was poured into water, extracted with ethyl acetate and the organic phase evaporated. The residue was recrystallised from a mixture of methylene chloride, methanol and hexane to give 4-[4'-(3-dimethylamino-2-hydroxypropoxy)anilino]6-(3'-methylanilino) pyrimidine in 54% yield, m.p. 192°–195° C.;

NMR Spectrum: ($CD_3SOCD_3+CD_3COOD$) 2.4 (s, 3H), 3.0 (s, 6H), 3.3 (m, 2H), 4.1 (d, 2H), 4.4 (m, 1H), 6.2 (s, 1H), 6.9 (d, 1H), 7.0(d, 2H), 7.3 (t, 1H), 7.4 (d, 2H), 7.5 (d, 2H), 8.3 (s, 1H);

Elemental Analysis: Found C, 66.5; H, 6.8; N, 17.3; $C_{22}H_{27}N_5O_2$0.25$H_2O$ requires C, 66.4; H, 6.9; N, 17.6%.

The 4-[4'-(2,3-epoxypropoxy)anilino]6-(3'-methylanilino)pyrimidine used as starting material was obtained as follows:

A mixture of 4-[4'-hydroxyanilino]6-(3'-methylanilino) pyrimidine (1.14 g), 1-bromo-2,3-epoxypropane-(0.5 ml) and potassium carbonate (1.24 g) in DMSO (12 ml) was stirred at ambient temperature for 16 hours to give 4-[4'-(2,3-epoxypropoxy)anilino]6-(3'-methylanilino) pyrimidine (0.70 g);

NMR Spectrum: (CD$_3$SOCD$_3$+CD$_3$COOD) 2.3 (s, 3H), 2.7 (m, 1H), 2.8 (t, 1H), 3.3 (m, 1H), 3.8 (m, 1H), 4.3 (m, 1H), 6.1 (s, 1H), 6.8 (d, 1H), 6.9 (m, 2H), 7.2 (t, 1H), 7.3 (d, 2H), 7.4 (d, 2H), 8.2 (s, 1H).

EXAMPLE 34

Using an analogous reaction procedure to that described in Example 6, 6-chloro-4-(3'-chloro-4'-fluoroanilino) pyrimidine (0.258 g) was reacted with 4-[N-(2-hydroxyethyl)-N-methylamino]aniline (0.166 g). The product so obtained was recrystallised from a mixture of methylene chloride, methanol and hexane to give 4-[3'-chloro-4'-fluoroanilino]6-[4'-{N-(2-hydroxyethyl)-N-methylamino}anilino]pyrimidine in 10% yield;

NMR Spectrum: (CD$_3$SOCD$_3$) 3.0 (s, 3H), 3.4 (d, 2H), 3.6 (d, 2H), 6.0 (s, 1H), 6.8 (d, 2H), 7.4 (m, 4H), 7.8 (m, 1H), 8.3 (s, 1H), 9.5 (s, 1H), 9.8 (s, 1H);

Elemental Analysis: Found C, 54.4; H, 5.1; N, 15.6; C$_{19}$H$_{20}$N$_5$CLFO requires C, 58.6, H, 5.1; N, 18.0%.

The 4-[N-(2-hydroxyethyl)-N-methylamino]aniline used as starting material was obtained as follows:

A mixture of 4-fluoronitrobenzene (2.8 g), 2-methylaminoethanol (5.0 g) and potassium t-butoxide (2.0 g) in DMF (50 ml) was heated and stirred at 60° C. for 16 hours. The mixture was poured into water, extracted with ethyl acetate and the organic phase evaporated. The residue was recrystallised from a mixture of ethyl acetate and hexane to give 4-nitro-[N-(2-hydroxyethyl)-N-methyl] aniline (2.4 g), m.p. 100°–102° C. The product so obtained was dissolved in ethyl acetate and hydrogenated in the presence of a 10% Pd/C catalyst to give 4-amino-[N-(2-hydroxyethyl)-N-methyl]aniline (1.8 g);

NMR Spectrum: (CD$_3$SOCD$_3$) 2.7 (s, 3H), 3.2 (t, 2H), 3.5 (m, 2H), 4.3 (s, 2H), 4.5 (t, 1H), 6.5 (s, 4H).

EXAMPLE 35

A mixture of 6-(3'-methylanilino)-4-[3'-(ethoxycarbonylmethoxy) anilino]pyrimidine (0.10 g) and diethanolamine (0.06 g) in ethanol (7 ml) was heated at reflux for 72 hours. The mixture was cooled and water (20 ml) added. The ethanol was evaporated and the solid filtered off to give 4-(3'-{N,N-di-(2-hydroxyethyl) carbamoylmethoxy}anilino]6-(3'-methylanilino)pyrimidine in 39% yield, m.p. 112°–113° C.;

NMR Spectrum: (CD$_3$SOCD$_3$) 2.30 (s, 3H), 2.48 (t, 1H), 3.25–3.70 (m, 7H), 4.65 (s, 1H), 4.83 (s, 2H), 4.95 (s, 1H), 6.19 (s, 1H), 6.52 (m, 1H), 6.80 (d, 1H), 7.0–7.4 (m, 6H), 8.37 (s, 1H), 9.02 (s, 1H), 9.07 (S, 1H).

EXAMPLE 36

Using an analogous reaction procedure to that described in Example 33, a mixture of 4-[3'-(2,3-epoxypropoxy) anilino]6-(3'-methylanilino) pyrimidine, 33% dimethylamine in ethanol and DMF was stirred overnight at ambient temperature. The reaction mixture was diluted with water and extracted with ethyl acetate. The product so obtained was washed with water and with brine, dried (MgSO$_4$) and evaporated. The residue was recrystallised from a mixture of methylene chloride, methanol and hexane to give 4-[3'-(3-dimethylamino-2-hydroxypropoxy)anilino]6-(3'-methylanilino)pyrimidine in 55% yield, m.p. 120°–122° C.;

NMR Spectrum: (CD$_3$SOCD$_3$) 2.25 (s, 6H), 2.28 (s, 3H), 3.78–3.98 (m, 3H), 4.89 (s, 1H), 6.18 (s, 1H), 6.53 (d, 1H), 6.8 (d, 1H), 7.03–7.38 (m, 7H), 8.27 (s, 1H), 9.05 (d, 2H);

Elemental Analysis: Found C, 66.4; H, 6.9; N, 16.9; C$_{22}$H$_{27}$N$_5$O$_2$0.4H$_2$O requires C, 66.0; H, 7.0; N, 17.5%.

The 4-[3'-(2,3-epoxypropoxy)anilino]6-(3'-methylanilino)pyrimidine used as starting material was prepared as follows;

A mixture of 4-[3'-hydroxyanilino]6-(3'-methylanilino) pyrimidine (1 g), 1-bromo-2,3-epoxypropane (0.44 ml) and potassium carbonate (0.95 g) in DMSO (12 ml) was stirred at ambient temperature overnight. The reaction mixture was diluted with water and extracted with methylene chloride. The organic layer was washed with water, dried (MgSO$_4$) and evaporated to give 4-[3'-(2,3-epoxypropoxy)anilino]6-(3'-methylanilino)pyrimidine in 38% yield, m.p. 143°–145° C.;

NMR Spectrum: (CD$_3$SOCD$_3$) 2.29 (s, 3H), 2.5 (m, 1H), 2.84 (m, 1H), 3.29–3.38 (m, 1H), 3.81 (m, 1H), 4.28 (m, 1H), 6.19 (s, 1), 6.56 (m, 1H), 6.8 (d, 1H), 7.04–7.21 (m, 3H), 7.28–7.48 (m, 3H), 8.25 (s, 1H), 9.01 (s, 1H), 9.09 (s, 1H).

EXAMPLE 37

Using an analogous reaction procedure to that described in Example 33, a mixture of 4-[3'-(2,3-epoxypropoxy) anilino]6-(3'-methylanilino) pyrimidine and 33% methylamine in ethanol and NHP was stirred over 2 days at room temperature. The reaction mixture was diluted with water and extracted with ethyl acetate. The product so obtained was washed with water and with brine, dried (MgSO$_4$) and evaporated. The residue was recrystallised from a mixture of methylene chloride, methanol and hexane to give 4-[3'-(3-methylamino-2-hydroxypropoxy)anilino]6-(3'-methylanilino) pyrimidine is 46% yield, m.p. 88°–90° C.;

NMR Spectrum: (CD$_3$SOCD$_3$) 2.28 (s, 3H), 2.32 (s, 3H), 2.58–2.63 (m, 2H), 3.82–3.96 (s, 1H), 6.17 (s, 1H), 56 (m, 1H), 6.79 (d, 1H), 7.08–7.35 (s, 1H), 8.28 (s, 1H), 9.03 (s, 1H), 9.07 (s, 1H);

Elemental Analysis: Found C, 64.3; H, 6.8; N, 16.5; C$_{21}$H$_{24}$N$_5$O$_2$ requires C, 66.5; H, 6.6; N, 18.5%.

EXAMPLE 38

A mixture of 6-(3'-methylanilino)-4-[3'-(ethoxycarbonylmethoxy) anilino]pyrimidine (0.10 g) and 2-(dimethylamino)ethylamine (0.05 g) in ethanol (5 ml) was stirred at ambient temperature for 40 hours. The volume of solvent was reduced by evaporation, and the product precipitated with water to give 6-(3'-methylanilino)-4-[3'-{N,N-(2-dimethylaminoethyl)carbamoylmethoxy}anilino] pyrimidine in 52% yield, m.p. 115°–120° C.;

NMR Spectrum: (CD$_3$SOCD$_3$) 2.13 (s, 6H), 2.2–2.4 (m, 5H), 3.21 (t, 2H), 4.44 (s, 2H), 6.00 (d, 1H), 6.19 (s, 1H), 6.56 (d, 1H), 7.05–7.40 (m, 6H), 7.90 (t, 1H), 8.28 (s, 1H), 9.02 (s, 1H), 9.11 (s, 1H);

Elemental Analysis: Found C, 60.1; H, 6.5; N, 17.0; C$_{23}$H$_{28}$N$_6$O$_2$1H$_2$CO$_3$ requires C, 60.1; H, 6.3; N, 17.4%.

EXAMPLE 39

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph.Eur | 182.75 |

| | | |
|---|---|---|
| Croscarmellose sodium | 12.0 | |
| Maize starch paste (5% w/v paste) | 2.25 | |
| Magnesium stearate | 3.0 | |
| (b) Tablet II | | mg/tablet |
| Compound X | 50 | |
| Lactose Ph.Eur | 223.75 | |
| Croscarmellose sodium | 6.0 | |
| Haize starch | 15.0 | |
| Polyvinylpyrrolidone (5% w/v paste) | 2.25 | |
| Magnesium stearate | 3.0 | |
| (c) Tablet III | | mg/tablet |
| Compound X | 1.0 | |
| Lactose Ph.Eur | 93.25 | |
| Croscarmellose sodium | 4.0 | |
| Maize starch paste (5% w/v paste) | 0.75 | |
| Magnesium stearate | 1.0 | |
| (d) Capsule | | mg/capsule |
| Compound X | 10 | |
| Lactose Ph.Eur | 488.5 | |
| Magnesium stearate | 1.5 | |
| (e) Injection I | | (50 mg/ml) |
| Compound X | 5.0% w/v | |
| 1 M Sodium hydroxide solution | 15.0% v/v | |
| 0.1 M Hydrochloric acid (to adjust pH to 7.6) | | |
| Polyethylene glycol 400 | 4.5% w/v | |
| Water for injection to 100% | | |
| (f) Injection II | | 10 mg/ml |
| Compound X | 1.0% w/v | |
| Sodium phosphate BP | 3.6% w/v | |
| 0.1 M Sodium hydroxide solution | 15.0% v/v | |
| Water for injection to 100% | | |
| (g) Injection III | | (1 mg/ml, buffered to pH 6) |
| Compound X | 0.1% w/v | |
| Sodium phosphate BP | 2.26% w/v | |
| Citric acid | 0.38% w/v | |
| Polyethylene glycol 400 | 3.5% w/v | |
| Water for injection to 100% | | |

Note

The above formulations may be obtained by conventional procedures well known in the pharmaceutical art. The tablets (a)–(c) may be enteric coated by conventional means, for example to provide a coating of cellulose acetate phthalate.

I claim:

1. A pharmaceutical composition which comprises a pyrimidine derivative of the formula I

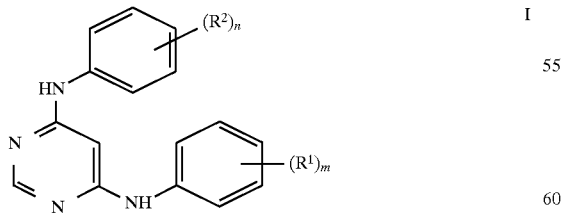

wherein m is 1, 2 or 3;

each $R^1$ is independently hydrogen, hydroxy, amino, nitro, halogeno, cyano, carboxy, carbamoyl, ureido, N-(1–4C)alkylcarbamoyl, N,N-di-[(1–4C)alkyl] carbamoyl, (1–4C)alkoxycarbonyl, (1–4C)alkyl, (1–4C)alkoxy, (1–3C)alkylenedioxy, (1–4C) alkylamino, di-[(1–4C)alkyl]amino, (1–4C)alkylthio, (1–4C)alkylsulphinyl, (1–4C)alkylsulphonyl, hydroxy-(1–4C)alkyl, (1–4C)alkoxy-(1–4C)alkyl, halogeno-(1–4C)alkyl, (2–4C)alkanoyloxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]carbamoyl-(1–4C)alkyl, amino-(1–4C)alkyl, (1–4C)alkylamino-(1–4C)alkyl, di-[(1–4C)alkyl]amino-(1–4C)alkyl, cyano-(1–4C)alkyl, hydroxy-(2–4C)alkoxy, (1–4C)alkoxy-(2–4C)alkoxy, halogeno-(1–4C)alkoxy, (2–4C)alkanoyloxy-(2–4C)alkoxy, carboxy-(1–4C)alkoxy, (1–4C)alkoxycarbonyl-(1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, N-[hydroxy-(2–4C)alkyl]carbamoyl-(1–4C)alkoxy, N,N-di-[hydroxy-(2–4C)alkyl]carbamoyl-(1–4C)alkoxy, amino-(2–4C)alkoxy, (1–4C)alkylamino-(2–4C)alkoxy, di-[(1–4C)alkyl]amino-(2–4C)alkoxy, N-[hydroxy-(2–4C)alkyl]amino-(2–4C)alkoxy, N,N-di-[hydroxy-(2–4C)alkyl]amino-(2–4C)alkoxy, N-[hydroxy-(2–4C)alkyl]N-[(1–4C)alkyl]amino-(2–4C)alkoxy, amino-(2–4C)alkoxy-(2–4C)alkoxy, N-[(1–4C)alkyl]amino-(2–4C)alkoxy-(2–4C)alkoxy N,N-di-[(1–4C)alkyl]amino-(2–4C)alkoxy-(2–4C)alkoxy, N-[hydroxy-(2–4C)alkyl]amino-(2–4C)alkoxy-(2–4C)alkoxy, N,N-di-[hydroxy-(2–4C)alkyl]amino-(2–4C)alkoxy-(2–4C)alkoxy, N-[hydroxy-(2–4C)alkyl]N-[(1–4C)alkyl]amino-(2–4C)alkoxy-(2–4C)alkoxy, amino-hydroxy-(2–4C)alkoxy, N-[(1–4C)alkyl]amino-hydroxy-(2–4C)alkoxy, N,N-di-[(1–4C)alkyl]amino-hydroxy-(2–4C)alkoxy, N-[hydroxy-(2–4C)alkyl] amino-hydroxy-(2–4C)alkoxy, N,N-di-[hydroxy-(2–4C)alkyl]amino-hydroxy-(2–4C)alkoxy, N-[hydroxy-(2–4C)alkyl]N-[(1–4C)alkyl]amino-hydroxy-(2–4C)alkoxy, amino-hydroxy-(2–4C)alkoxy-(2–4C)alkoxy, N-[(1–4C)alkyl]amino-hydroxy-(2–4C)alkoxy-(2–4C)alkoxy, N,N-di-[(1–4C)alkyl]amino-hydroxy-(2–4C)alkoxy-(2–4C)alkoxy, N-[hydroxy-(2–4C)alkyl]amino-hydroxy-(2–4C)alkoxy-(2–4C) alkoxy, N,N-di-[hydroxy-(2–4C)alkyl]amino-hydroxy-(2–4C)alkoxy-(2–4C)alkoxy, di-hydroxy-(2–4C) alkoxy, (1–4C)alkoxy-hydroxy-(2–4C)alkoxy, hydroxy-(2–4C)alkoxy-hydroxy-(2–4C)alkoxy, di-hydroxy-(2–4C)alkoxy-(2–4C)alkoxy, (1–4C)alkoxy-hydroxy-(2–4C)alkoxy-(2–4C)alkoxy, hydroxy-(2–4C)alkoxy-hydroxy-(2–4C)alkoxy-(2–4C) alkoxy, N-[amino-(2–4C)alkyl]carbamoyl-(1–4C) alkoxy, N-[N-{(1–4C)alkyl}amino-(2–4C)alkyl] carbamoyl-(1–4C)alkoxy, N-[N,N-di-{(1–4C) alkyl}amino-(2–4C)alkyl]carbamoyl-(1–4C)alkoxy, N-[N-{hydroxy-(2–4C)alkyl}amino-(2–4C)alkyl] carbamoyl-(1–4C)alkoxy, N-[N-{hydroxy-(2–4C) alkyl}-N-1{(1–4C)alkyl}amino-(2–4C)alkyl] carbamoyl-(1–4C) alkoxy, N-[di-{hydroxy-(2–4C) alkyl}amino-(2–4C)alkyl]carbamoyl-(1–4C)alkoxy, N-[amino-(2–4C)alkyl]carbamoyl-(1–4C)alkoxy (2–4C)alkoxy, N-[N-{(1–4C)alkyl}amino-(2–4C) alkyl]carbamoyl-(1–4C)alkoxy(2–4C)alkoxy, N-[N,N-di-{(1–4C)alkyl}amino-(2–4C)alkyl]carbamoyl-(1–4C)alkoxy(2–4C)alkoxy, N-[N-{hydroxy-(2–4C) alkyl}amino-(2–4C)alkyl]carbamoyl-(1–4C)alkoxy (2–4C)alkoxy, N-[N-{hydroxy-(2–4C)alkyl}-N-{(1 14C)alkyl}amino-(2–4C)alkyl]carbamoyl-(1–4C) alkoxy-(2–4C)alkoxy, N-[N,N-di-{hydroxy-(2–4C) alkyl}amino-(2–4C)alkyl]carbamoyl-(1–4C) alkoxy-(2–4C)alkoxy, (2–4C)alkanoyloxy, (2–4C)

alkanoylamino, N-[hydroxy-(2–4C)alkyl]amino, N-[hydroxy-(2–4C)alkyl]N-[(1–4C)alkyl]amino or (1–4C)alkylsulphonylamino;

n is 1, 2 or 3; and each $R^2$ is independently hydrogen, hydroxy, halogeno, trifluoromethyl, trifluoromethoxy, amino, nitro, cyano, (1–4C)alkyl, (1–4C)alkoxy, (1–4C)alkylamino, di-[(1–4C)alkyl]amino, (1–4C)alkylthio, (1–4C)alkylsulphinyl, (1–4C)alkylsulphonyl, (2–4C)alkanoylamino, (2–4C)alkanoyl or (1–3C)alkylenedioxy; or a pharmaceutically acceptable salt thereof, in association with a pharmaceutically-acceptable diluent or carrier.

2. A pharmaceutical composition which comprises a pyrimidine derivative of the formula I as claimed in claim 1 wherein m is 1, 2 or 3 and each $R^1$ is independently hydrogen, hydroxy, amino, halogeno, cyano, carboxy, carbamoyl, ureido, (1–4C)alkoxycarbonyl, (1–4C)alkyl, (1–4C)alkoxy, (1–3C)alkylenedioxy, (1–4C)alkylamino, di-[(1–4C)alkyl]amino, (1–4C)alkylthio, halogeno-(1–4C)alkyl, (1–4C)alkoxy-(1–4C)alkyl, (1–4C)alkylamino-(1–4C)alkyl, di-[(1–4C)alkyl]amino-(1–4C)alkyl, cyano-(1–4C)alkyl, halogeno-(1–4C)alkoxy, hydroxy-(2–4C)alkoxy, (1–4C)alkoxy-(2–4C)alkoxy, (1–4C)alkoxycarbonyl-(1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, N-[hydroxy-(2–4C)alkyl]carbamoyl-(1–4C)alkoxy, N,N-di-[hydroxy-(2–4C)alkyl]carbamoyl-(1–4C)alkoxy, (1–4C)alkylamino-(2–4C)alkoxy, di-[(1–4C)alkyl]amino-(2–4C)alkoxy, (2–4C)alkanoylamino, N-[hydroxy-(2–4C)alkyl]amino, N-[hydroxy-(2–4C)alkyl]N-[(1–4C)alkyl]amino, (1–4C)alkylamino-hydroxy-(2–4C)alkoxy, di-[(1–4C)alkyl]amino-hydroxy-(2–4C)alkoxy, N-[amino-(2–4C)alkyl]carbamoyl-(1–4C)alkoxy, N-[N-{(1–4C)alkyl}amino-(2–4C)alkyl]carbamoyl-(1–4C)alkoxy or N-[N,N-di-{(1 4C)alkyl}amino-(2–4C)alkyl]carbamoyl-(1–4C)alkoxy;

n is 1,2 or 3 and each $R^2$ is independently hydrogen, hydroxy, halogeno, trifluoromethyl, trifluoromethoxy, amino, nitro, cyano, (1–4C)alkyl, (1–4C)alkoxy, (1 4C)alkylamino, di-[(1–4C)alkyl]amino, (1–4C)alkylthio, (1–4C)alkylsulphinyl, (1–4C)alkylsulphonyl, (2–4C)alkanoylamino, (2–4C)alkanoyl or (1–3C)alkylenedioxy;

or a pharmaceutically-acceptable salt thereof, in association with a pharmaceutically-acceptable diluent or carrier.

3. A pharmaceutical composition which comprises a pyrimidine derivative of the formula I as claimed in claim 1 wherein m is 1 or 2 and each $R^1$ is independently hydrogen, hydroxy, amino, halogeno, cyano, carboxy, carbamoyl, ureido, (1–4C)alkoxycarbonyl, (1–4C)alkyl, (1–4C)alkoxy, (1–3C)alkylenedioxy, (1–4C)alkylamino, di-[(1–4C)alkyl]amino, halogeno-(1–4C)alkyl, cyano-(1–4C)alkyl, halogeno-(1–4C)alkoxy, hydroxy-(2–4C)alkoxy, (1–4C)alkoxy-(2–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, N-[hydroxy-(2–4C)alkyl]carbamoyl-(1–4C)alkoxy, N,N-di-[hydroxy-(2–4C)alkyl]carbamoyl-(1–4C)alkoxy, (1–4C)alkylamino-(2–4C)alkoxy, di-[(1–4C)alkyl]amino-(2–4C)alkoxy, (2–4C)alkanoylamino, N-[hydroxy-(2–4C)alkyl]amino, N-[hydroxy-(2–4C)alkyl]N-[(1–4C)alkyl]amino, (1–4C)alkylamino-hydroxy-(2–4C)alkoxy, di-[(1–4C)alkyl]amino-hydroxy-(2–4C)alkoxy, N-[amino-(2–4C)alkyl]carbamoyl-(1–4C)alkoxy, N[N-{(1–4C)alkyl}amino-(2–4C)alkyl]carbamoyl-(1–4C)alkoxy or N-[N,N-di-{(1–4C)alkyl}amino-(2–4C)alkyl]carbamoyl-(1–4C)alkoxy;

n is 1, 2 or 3 and each $R^2$ is independently hydrogen, hydroxy, halogeno, trifluoromethyl, trifluoromethoxy, amino, nitro, cyano, (1–4C)alkyl, (1–4C)alkoxy, (1–4C)alkylamino, di-[(1–4C)alkyl)amino, (1–4C)alkylthio, (1–4C)alkylsulphinyl, (1–4C)alkylsulphonyl, (2–4C)alkanoylamino, (2–4C)alkanoyl or (1–3C)alkylenedioxy;

or a pharmaceutically-acceptable salt thereof, in association with a pharmaceutically-acceptable diluent or carrier.

4. A pharmaceutical composition which comprises a pyrimidine derivative of the formula I as claimed in claim 1 wherein m is 1 or 2 and each $R^1$ is independently hydrogen, hydroxy, amino, fluoro, chloro, bromo, trifluoromethyl, trifluoromethoxy, cyano, methyl, ethyl, methoxy, ethoxy, methylenedioxy, methylamino, ethylamino, dimethylamino, diethylamino, 2-hydroxyethoxy, 3-hydroxypropoxy, 2-methoxyethoxy, 2-ethoxyethoxy, 3-methoxypropoxy, methoxycarbonylmethoxy, ethoxycarbonylmethoxy, cyanomethoxy, carbamoylmethoxy, N-methylcarbamoylmethoxy, N,N-dimethylcarbamoylmethoxy, 2-(methylamino)ethoxy, 2-(ethylamino)ethoxy, 3-(methylamino)propoxy, 3-(ethylamino)propoxy, 2-(dimethylamino)ethoxy, 2-(diethylamino)ethoxy, 3-(dimethylamino)propoxy, 3-(diethylamino)propoxy, acetamido, N-(2-hydroxyethyl)carbamoylmethoxy, 2[N-(2-hydroxyethyl)carbamoyl]ethoxy, N,N-di-(2-hydroxyethyl)carbamoylmethoxy, 2-[N,N-di-(2-hydroxyethyl)carbamoyl]ethoxy, N-(2-hydroxyethyl)amino, N-(3-hydroxypropyl)amino, N-(2-hydroxyethyl)-N-methylamino, N-(3-hydroxypropyl)-N-ethylamino, 3-amino-2-hydroxypropoxy, 3-methylamino-2-hydroxypropoxy, 3-dimethylamino-2-hydroxypropoxy, N-(2-aminoethyl)carbamoylmethoxy, 2[N-(2-aminoethyl)carbamoyl]ethoxy, N-(2-methylaminoethyl)carbamoylmethoxy, 2-[N-(2-methylaminoethyl)carbamoyl]ethoxy, N-(2-dimethylaminoethyl)carbamoylmethoxy or 2[N-(2-dimethylaminoethyl)carbamoyl]ethoxy; and n is 1 or 2 and each $R^2$ is independently hydrogen, hydroxy, fluoro, chloro, bromo, trifluoromethyl, trifluoromethoxy, cyano, methyl, ethyl, methoxy or ethoxy;

or a pharmaceutically-acceptable salt thereof, in association with a pharmaceutically-acceptable diluent or carrier.

5. A pharmaceutical composition which comprises a pyrimidine derivative of the formula I

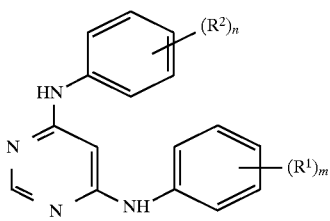

wherein m is 1 or 2 and each $R^1$ is independently hydrogen, hydroxy, fluoro, chloro, methyl, methoxy, dimethylamino, 2-hydroxyethoxy, 3-hydroxypropoxy, 2-methoxyethoxy, methoxycarbonylmethoxy, ethoxycarbonylmethoxy, cyanomethoxy, carbamoylmethoxy, N-methylcarbamoylmethoxy, N,N-dimethylcarbamoylmethoxy, 2-(dimethylamino)ethoxy, 3-(dimethylamino)propoxy, N-(2-hydroxyethyl)carbamoylmethoxy, N,N-di-(2-hydroxyethyl)carbamoylmethoxy, N-(2-hydroxyethyl)-N-methylamino, 3-methylamino-2-hydroxypropoxy, 3-dimethylamino-2-hydroxypropoxy or N-(2-dimethylaminoethyl)carbamoylmethoxy; and n is 1 or 2 and each $R^2$ is independently fluoro, chloro, bromo, trifluoromethyl, methyl or ethyl;

or a pharmaceutically-acceptable acid-addition salt thereof, in association with a pharmaceutically-acceptable diluent or carrier.

6. A pharmaceutical composition which comprises a pyrimidine derivative of the formula I

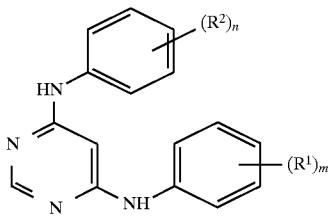

wherein m is 1 and $R^1$ is independently hydrogen, hydroxy, fluoro, chloro, methyl, methoxy, dimethylamino, 2-hydroxyethoxy, 3-hydroxypropoxy, 2-methoxyethoxy, methoxycarbonylmethoxy, ethoxycarbonylmethoxy, cyanomethoxy, carbamoylmethoxy, N-methylcarbamoylmethoxy, N,N-dimethylcarbamoylmethoxy, 2-dimethylaminoethoxy, 3-dimethylaminopropoxy, N-(2-hydroxyethyl)carbamoylmethoxy, N,N-di-(2-hydroxyethyl)carbamoylmethoxy, N-(2-hydroxyethyl)-N-methylamino, 3-methylamino-2-hydroxypropoxy, 3-dimethylamino-2-hydroxypropoxy or N-(2-dimethylaminoethyl)carbamoylmethoxy; and n is 1 or 2 and each $R^2$ is independently fluoro, chloro or methyl;

or a pharmaceutically-acceptable acid-addition salt thereof, in association with a pharmaceutically-acceptable diluent or carrier.

7. A pharmaceutical composition which comprises a pyrimidine derivative, or a pharmaceutically-acceptable acid addition salt thereof, selected from:

4-(3'-chloro-4'-fluoroanilino)-6-(4'-methoxyanilino)pyrimidine, 4-(3'-chloro-4'-fluoroanilino)-6-(4'-dimethaminoanilino)pyrimidine, 4-(3'-chloro-4'-fluoroanilino)-6-[4'-(2-hydroxyethoxy)anilino]pyrimidine, 4,6-di-(3'-methylanilino)pyrimidine, 4-[4'-(carbamoylmethoxy)anilino]6-(3'-chloro-4'-fluoroanilino)pyrimidine, 4-(3'-chloro-4'-fluoroanilino)-6-(4'-N,N-dimethylcarbamoylmethoxy)anilino]pyrimidine, 4-[4'-(2-hydroxyethoxy)anilino]6-(3'-methylanilino)pyrimidine, 4-[4'-(2-dimethylaminoethoxy)anilino]6-(3'-methylanilino)pyrimidine, 4-[4'-(3-dimethylaminopropoxy)anilino]-6-(3'-methylanilino)pyri-midine, 4-(3'-chloro-4'-fluoroanilino)-6-[4-{N-(2-hydroxyethyl)carbamoylmethoxy}anilino]pyrimidine, 4-[4'-{N-(2-dimethylaminoethyl)carbamoylmethoxy}anilino]-6-(3'-methylanilino)pyrimidine, or, 4-[4'-(3-dimethylamino-2-hydroxypropoxy)anilino]6-(3'-methylanilino)pyrimidine, in association with a pharmaceutically-acceptable diluent or carrier.

8. A method for producing an anti-cancer effect by providing an anti-proliferative effect in a warm blooded animal having a cancer which is sensitive to inhibition of Class I receptor tyrosine kinase enzymes which comprises administering to said animal an effective amount of a pyrimidine derivative of the formula I, or a pharmaceutically acceptable salt thereof, as claimed in any one of claims 1 to 7.

9. A method for producing in a warm blooded animal an inhibitory effect against Class I receptor tyrosine kinase enzymes which comprises administering to said animal an effective amount of a pyrimidine derivative of the formula I, or a pharmaceutically acceptable salt thereof, as claimed in any one of claims 1 to 7.

10. A pyrimidine derivative of the formula I

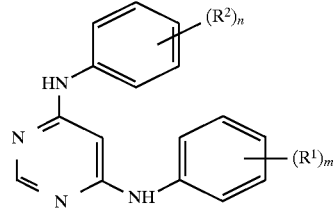

wherein m is 1, 2 or 3;

each $R^1$ is independently hydroxy, carboxy, carbamoyl, ureido, N-(1–4C)alkylcarbamoyl, N,N-di-[(1–4C)alkyl]carbamoyl, (1–3C)alkylenedioxy, (1–4C)alkylsulphonyl, hydroxy-(1–4C)alkyl, (2–4C)alkanoyloxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]carbamoyl-(1–4C)alkyl, amino-(1–4C)alkyl, (1–4C)alkylamino-(1–4C)alkyl, di-[(1–4C)alkyl]amino-(1–4C)alkyl, cyano-(1–4C)alkyl, hydroxy-(2–4C)alkoxy, (1–4C)alkoxy-(2–4C)alkoxy, (2–4C)alkanoyloxy-(2–4C)alkoxy, carboxy-(1–4C)alkoxy, (1–4C)alkoxycarbonyl-(1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, N-[hydroxy-(2–4C)alkyl]carbamoyl-(1–4C)alkoxy, N,N-di-[hydroxy-(2–4C)alkyl]carbamoyl-(1–4C)alkoxy, amino-(2–4C)alkoxy, (1–4C)alkylamino-(2–4C)alkoxy, di-[(1–4C)alkyl]amino-(2–4C)alkoxy, N-[hydroxy-(2–4C)alkyl]amino- (2–4C)alkoxy, N,N-di-[hydroxy-(2–4C)alkyl]amino-(2–4C)alkoxy, N-[hydroxy-(2–4C)alkyl]N-[(1–4C)alkyl]amino-(2–4C)alkoxy, amino-(2–4C)alkoxy-(2–4C)alkoxy, N-[(1–4C)alkyl]amino-(2–4C)alkoxy-(2–4C)alkoxy N,N-di-[(1–4C)alkyl]amino-(2–4C)alkoxy-(2–4C)alkoxy, N-[hydroxy-(2–4C)alkyl]amino-(2–4C)alkoxy-(2–4C)alkoxy, N,N-di-[hydroxy-(2–4C)alkyl]amino-(2–4C)alkoxy-(2–4C)alkoxy, N-[hydroxy-(2–4C)alkyl]N-[(1–4C)alkyl]amino-(2–4C)alkoxy-(2–4C)alkoxy, amino-hydroxy-(2–4C)alkoxy, N-[(1–4C)alkyl]amino-hydroxy-(2–4C)alkoxy, N,N-di-[(1–4C)alkyl]amino-hydroxy-(2–4C)alkoxy, N-[hydroxy-(2–4C)alkyl]amino-hydroxy-(2–4C)alkoxy, N,N-di-[hydroxy-(2–4C)alkyl]amino-hydroxy-(2–4C)alkoxy, N-[hydroxy-(2–4C)alkyl]N-[(1–4C)alkyl]amino-hydroxy-(2–4C)alkoxy, amino-hydroxy-(2–4C)alkoxy-(2–4C)alkoxy, N-[(1–4C)alkyl]amino-hydroxy-(2–4C)alkoxy-(2–4C)alkoxy, N,N-di-[(1–4C)alkyl]amino-hydroxy-(2–4C)alkoxy-(2–4C)alkoxy, N-[hydroxy-(2–4C)alkyl]amino-hydroxy-(2–4C)alkoxy-(2–4C)alkoxy, N,N-di-[hydroxy-(2–4C)alkyl]amino-hydroxy-(2–4C)alkoxy-(2–4C)alkoxy, di-hydroxy-(2–4C)alkoxy, (1–4C)alkoxy-hydroxy-(2–4C)alkoxy, hydroxy-(2–4C)alkoxy-hydroxy-(2–4C)alkoxy, di-hydroxy-(2–4C)alkoxy-(2–4C)alkoxy, (1–4C)alkoxy-hydroxy-(2–4C)alkoxy-(2–4C)alkoxy, hydroxy-(2–4C)alkoxy-hydroxy-(2–4C)alkoxy-(2–4C)alkoxy, N-[amino-(2–4C)alkyl]carbamoyl-(1–4C)alkoxy, N[N-{(1–4C)alkyl}amino-(2–4C)alkyl]carbamoyl-(1–4C)alkoxy, N-[N,N-di-{(1–4C)alkyl}amino-(2–4C)alkyl]carbamoyl-(1–4C)alkoxy, N[N-{hydroxy-(2–4C)alkyl}amino-(2–4C)alkyl]carbamoyl-(1–4C)alkoxy, N[N-{hydroxy-(2–4C)alkyl}-N-{(1–4C)alkyl}amino-(2–4C)alkyl]carbamoyl-(1–4C)alkoxy, N-[di-{hydroxy-(2–4C)alkyl}amino-(2–4C)alkyl]carbamoyl-(1–4C)alkoxy, N-[amino-(2–4C)alkyl]carbamoyl-(1–4C)alkoxy-(2–4C)alkoxy, N[N-{(1–4C)alkyl}amino-(2–4C)alkyl]carbamoyl-(1–4C)alkoxy-(2–4C)alkoxy, N-[N,N-di-{(1–4C)alkyl}amino-(2–4C)alkyl]carbamoyl-(1–4C)alkoxy-(2–4C)alkoxy, N-[N-{hydroxy-(2–4C)alkyl}amino-(2–4C)alkyl]carbamoyl-(1–4C)alkoxy-(2–4C)alkoxy, N[N-{hydroxy-(2–4C)alkyl}-N-{(1–4C)alkyl}amino-(2–4C)alkyl]carbamoyl-(1–4C)alkoxy-(2–4C)alkoxy, N-[N,N-di-{hydroxy-(2–4C)alkyl}amino-(2–4C)alkyl]caramoyl-(1–4C) alkoxy-(2–4C)alkoxy, (2–4C)alkanoyloxy, (2–4C)alkanoylamino, N-[hydroxy-(2–4C)alkyl]amino, N-[hydroxy-(2–4C)alkyl]N-[(1–4C)alkyl]amino or (1–4C)alkylsulphonylamino;

n is 1,2 or 3; and each $R^2$ is independently hydrogen, hydroxy, trifluoromethoxy, amino, cyano, (1–4C)alkyl, (1–4C)alkoxy, (1–4C)alkylamino, di-[(1–4C)alkyl]amino, (1–4C)alkylthio, (1–4C)alkylsulphinyl, (1–4C)alkylsulphonyl, (2–4C)alkanoylaamino, (2–4C)alkanoyl or (1–3C)alkylenedioxy;

or a pharmaceutically acceptable salt thereof.

11. A pyrimidine derivative of the formula I

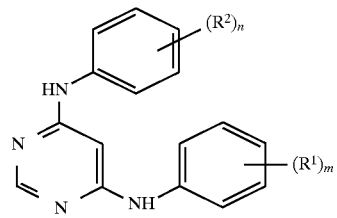

wherein m is 1, 2 or 3;

each $R^1$ is independently hydrogen, hydroxy, amino, halogeno, cyano, carboxy, carbamoyl, ureido, N-(1–4C)alkylcarbamoyl, N,N-di-[(1 4C)alkyl)]carbamoyl, (1–4C)alkoxycarbonyl, (1–4C)alkyl, (1–4C)alkoxy, (1–3C)alkylenedioxy, (1–4C)alkylthio, (1–4C)alkylsulphinyl, (1–4C)alkylsulphonyl, hydroxy-(1–4C)alkyl, (1–4C)alkoxy-(1–4C)alkyl, (2–4C)alkanoyloxy-(1–4C)alkyl, carboxy-(1–4C)alkyl, (1–4C)alkoxycarbonyl-(1–4C)alkyl, carbamoyl-(1 4C)alkyl, N-(1–4C)alkylcarbamoyl-(1–4C)alkyl, N,N-di-[(1–4C)alkyl]carbamoyl-(1–4C)alkyl, amino-(1–4C)alkyl, (1–4C)alkylamino-(1–4C)alkyl, di-[(1–4C)alkyl]amino-(1–4C)alkyl, cyano-(1–4C)alkyl, hydroxy-(2–4C)alkoxy, (1–4C)alkoxy-(2–4C)alkoxy, halogeno-(1–4C)alkoxy, (2–4C)alkanoyloxy-(2–4C)alkoxy, carboxy-(1–4C)alkoxy, (1–4C)alkoxycarbonyl-(1 4C)alkoxy, cyano-(1–4C)alkoxy, carbamoyl-(1 4C)alkoxy, N-(1–4C)alkylcarbamoyl-(1–4C)alkoxy, N,N-di-[(1 4C)alkyl]carbamoyl-(1–4C)alkoxy, N-hydroxy-(2–4C)alkyl]carbamoyl-(1–4C)alkoxy, N,N-di-[hydroxy-(1–4C)alkyl]carbamoyl-(1–4C)alkoxy, amino-(2–4C)alkoxy, (1–4C)alkylamino-(2–4C)alkoxy, di-[(1–4C)alkyl]amino-(2–4C)alkoxy, N-[hydroxy-(2–4C)alkyl]amino-(2–4C)alkoxy, N,N-di-[hydroxy-(2–4C)alkyl]amino-(2–4C)alkoxy, N-[hydroxy-(2–4C)alkyl]N-[(1–4C)alkyl)amino-(2–4C)alkoxy, amino-(2–4C)alkoxy-(2–4C)alkoxy, N-[(1–4C)alkyl]amino-(2–4C)alkoxy-(2–4C)alkoxy N,N-di-[(1–4C)alkyl]amino-(2–4C)alkoxy-(2–4C)alkoxy, N-[hydroxy-(2–4C) alkyl]amino-(2–4C)alkoxy-(2–4C)alkoxy, N,N-di-[hydroxy-(2–4C)alkyl]amino-(2–4C)alkoxy-(2–4C)alkoxy, N-[hydroxy-(2–4C)alkyl]N-[(1–4C)alkyl]amino-(2–4C)alkoxy-(2–4C)alkoxy, amino-hydroxy-(2–4C)alkoxy, N-[(1–4C)alkyl]amino-hydroxy-(2–4C)alkoxy, N,N-di-[(1–4C)alkyl]amino-hydroxy-(2–4C)alkoxy, N-[hydroxy-(2–4C)alkyl]amino-hydroxy-(2–4C)alkoxy, N,N-di-[hydroxy-(2–4C)alkyl]amino-hydroxy-(2–4C)alkoxy, N-[hydroxy-(2–4C)alkyl]N-[(1–4C)alkyl]amino-hydroxy-(2–4C)alkoxy, amino-hydroxy-(2–4C)alkoxy-(2–4C)alkoxy, N-[(1–4C)alkyl]amino-hydroxy-(2–4C)alkoxy-(2–4C)alkoxy, N,N-di-[(1–4C)alkylamino-hydroxy-(2–4C)alkoxy-(2–4C)alkoxy, N-[hydroxy-(2–4C)alkyl]amino-hydroxy-(2–4C)alkoxy-(2–4C)alkoxy, N,N-di-[hydroxy-(2–4C)alkyl]amino-hydroxy-(2–4C)alkoxy-(2–4C)alkoxy, di-hydroxy-(2–4C)alkoxy, (1–4C)alkoxy-hydroxy-(2–4C)alkoxy, hydroxy-(2–4C)alkoxy-hydroxy-(2–4C)alkoxy, di-hydroxy-(2–4C)alkoxy-(2–4C)alkoxy, (1–4C)alkoxy-hydroxy-(2–4C)alkoxy-(2–4C)alkoxy, hydroxy-(2–4C)alkoxy-hydroxy-(2–4)alkoxy-(2–4C)

alkoxy, N-[amino-(2–4C)alkyl]carbamoyl-(1–4C) alkoxy, N-N-{(1–4C)alkyl}amino-(2–4C)alkyl]carbamoyl-(1–4C)alkoxy, N-[N,N-di-{(1–4C)alkyl}amino-(2–4C)alkyl]carbamoyl-(1–4C)alkoxy, N-[N-{hydroxy-(2–4C)alkyl}amino-(2–4C)alkyl]carbamoyl-(1–4C)alkoxy, N[N-{hydroxy-(2–4C)alkyl}-N-{(1–4C)alkyl}amino-(2–4C)alkyl]carbamoyl-(1–4C)alkoxy, N-[di-{hydroxy-(2–4C)alkyl}amino-(2–4C)alkyl]carbamoyl-(1–4C)alkoxy, N-[amino-(2–4C)alkyl]carbamoyl-(1–4C)alkoxy-(2–4C)alkoxy, N[N-{(1–4C)alkyl}amino-(2–4C)alkyl]carbamoyl-(1–4C)alkoxy(2–4C)alkoxy, N-LN,N-di-{(1–4C)alkyl}amino-(2–4C)alkyl]carbamoyl-(1–4C)alkoxy(2–4C)alkoxy, N-N-{hydroxy-(2–4C)alkyl}amino-(2–4C)alkyl]carbamoyl-(1–4C)alkoxy (2–4C)alkoxy, N[N-{hydroxy-(2–4C)alkyl}-N-{(1–4C)alkyl}amino-(2–4C)alkyl]carbamoyl-(1–4C)alkoxy-(2–4C)alkoxy, N-[N,N-di-{hydroxy-(2–4C)alkyl}amino-(2–4C)alkyl]carbamoyl-(1–4C) alkoxy-(2–4C)alkoxy, (2–4C)alkanoyloxy, (2–4C)alkanoylamino, N-[hydroxy-(2–4C)alkyl]amino, N-[hydroxy-(2–4C)alkyl]N-[(1–4C)alkyl]amino or (1–4C)alkylsulphonylamino;

n is 1 ,2 or 3; and each $R^2$ is independently hydroxy, (1–4C)alkylsulphonyl, (2–4C)alkanoylamino, (2–4C)alkanoyl or (1–3C)alkylenedioxy;

or a pharmaceutically acceptable salt thereof.

12. A pyrimidine derivative of the formula I as claimed in claim 10 wherein m is 1, 2 or 3 and each $R^1$ is independently hydroxy, carboxy, carbamoyl, ureido, (1–3C)alkylenedioxy, (1–4C)alkylamino-(1–4C)alkyl, di-[(1–4C)alkyl]amino-(1–4C)alkyl, cyano-(1–4C)alkyl, hydroxy-(2–4C)alkoxy, (1–4C)alkoxy-(2–4C)alkoxy, (1–4C)alkoxycarbonyl-(1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, N-[hydroxy-(2–4C)alkyl]carbamoyl-(1–4C)alkoxy, N,N-di-[hydroxy-(2–4C)alkyl]carbamoyl-(1–4C)alkoxy, (1–4C)alkylamino-(2–4C)alkoxy, di-[(1–4C)alkyl]amino-(2–4C)alkoxy, (2–4C)alkanoylamino, N-[hydroxy-(2–4C)alkyl]amino, N-[hydroxy-(2–4C)alkyl]N-[(1–4C)alkyl]amino, (1–4C)alkylamino-hydroxy-(2–4C)alkoxy, di-[(1–4C)alkyl]amino-hydroxy-(2–4C)alkoxy, N-[amino-(2–4C)alkyl]carbamoyl-(1–4C)alkoxy, N-[N-{(1–4C)alkyl}amino-(2–4C)alkyl]carbamoyl-(1–4C)alkoxy or N-[N,N-di-{(1–4C)alkyl}amino-(2–4C)alkyl]carbamoyl-(1–4C)alkoxy;

n is 1, 2 or 3 and each $R^2$ is independently hydrogen, hydroxy, trifluoromethoxy, amino, cyano, (1–4C)alkyl, (1–4C)alkoxy, (1–4C)alkylamino, di-[(1–4C)alkyl]amino, (1–4C)alkylthio, (1–4C)alkylsulphinyl, (1–4C)alkylsulphonyl, (2–4C)alkanoylamino, (2–4C)alkanoyl or (1–3C)alkylenedioxy;

or a pharmaceutically-acceptable salt thereof.

13. A pyrimidine derivative of the formula I as claimed in claim 11 wherein m is 1, 2 or 3 and each $R^1$ is independently hydrogen, hydroxy, amino, halogeno, cyano, carboxy, carbamoyl, ureido, (1–4C)alkoxycarbonyl, (1–4C)alkyl, (1–4C)alkoxy, (1–3C)alkylenedioxy, (1–4C)alkylthio, (1–4C)alkoxy-(1–4C)alkyl, (1–4C)alkylamino-(1–4C)alkyl, di-[(1–4C)alkyl]amino-(1–4C)alkyl, cyano-(1–4C)alkyl, halogeno-(1–4C)alkoxy, hydroxy-(2–4C)alkoxy, (1–4C)alkoxy-(2–4C)alkoxy, (1–4C)alkoxycarbonyl-(1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, N-[hydroxy-(2–4C)alkyl]carbamoyl-(1–4C)alkoxy, N,N-di-[hydroxy-(2–4C)alkyl]carbamoyl-(1–4C)alkoxy, (1–4C)alkylamino-(2–4C)alkoxy, di-[(1–4C)alkyl]amino-(2–4C)alkoxy, (2–4C)alkanoylamino, N-[hydroxy-(2–4C)alkyl]amino, N-[hydroxy-(2–4C)alkyl]N-[(1–4C)alkyl]amino, (1–4C)alkylamino-hydroxy-(2–4C)alkoxy, di-[(1–4C)alkyl]amino-hydroxy-(2–4C)alkoxy, N-[amino-(2–4C)alkyl]carbamoyl-(1–4C)alkoxy, N-[N-{(1–4C)alkyl}amino-(2–4C)alkyl]carbamoyl-(1–4C)alkoxy or N-[N,N-di-{(1–4C)alkyl}amino-(2–4C)alkyl]carbamoyl-(1–4C)alkoxy;

n is 1, 2 or 3 and each R2is independently hydroxy, (1–4C)alkylsulphonyl, (2–4C)alkanoylamino, (2–4C)alkanoyl or (1–3C)alkylenedioxy;

or a pharmaceutically-acceptable salt thereof.

14. A pyrimidine derivative of the formula I as claimed in claim 10 wherein m is 1 or 2 and each $R^1$ is independently hydroxy, carboxy, carbamoyl, ureido, (1–3C)alkylenedioxy, cyano-(1–4C)alkyl, hydroxy-(2–4C)alkoxy, (1–4C)alkoxy-(2–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, N-[hydroxy-(2–4C)alkyl]carbamoyl-(1–4C)alkoxy, N,N-di-[hydroxy-(2–4C)alkyl]carbamoyl-(1–4C)alkoxy, (1–4C)alkylamino-(2–4C)alkoxy, di-[(1–4C)alkyl]amino-(2–4C)alkoxy, (2–4C)alkanoylamino, N-[hydroxy-(2–4C)alkyl]amino, N-[hydroxy-(2–4C)alkyl]N-[(1–4C)alkyl]amino, (1–4C)alkylamino-hydroxy-(2–4C)alkoxy, di-[(1–4C)alkyl]amino-hydroxy-(2–4C)alkoxy, N-[amino-(2–4C)alkyl]carbamoyl-(1–4C)alkoxy, N[N-{(1–4C)alkyl}amino-(2–4C)alkyl]carbamoyl-(1–4C)alkoxy or N-[N,N-di-{(1–4C)alkyl}amino-(2–4C)alkyl]carbamoyl-(1–4C)alkoxy;

n is 1, 2 or 3 and each $R^2$ is independently hydrogen, hydroxy, trifluoromethoxy, amino, cyano, (1–4C)alkyl, (1–4C)alkoxy, (1–4C)alkylamino, di-[(1–4C)alkyl]amino, (1–4C)alkylthio, (1–4C)alkylsulphinyl, (1–4C)alkylsulphonyl, (2–4C)alkanoylamino, (2–4C)alkanoyl or (1–3C)alkylenedioxy;

or a pharmaceutically-acceptable salt thereof.

15. A pyrimidine derivative of the formula I as claimed in claim 11 wherein m is 1 or 2 and each $R^1$ is independently hydrogen, hydroxy, amino, halogeno, cyano, carboxy, carbamoyl, ureido, (1–4C)alkoxycarbonyl, (1–4C)alkyl, (1–4C) alkoxy, (1–3C)alkylenedioxy, cyano-(1–4C)alkyl, halogeno-(1–4C)alkoxy, hydroxy-(2–4C)alkoxy, (1–4C)alkoxy-(2–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]carbamoyl-(1–4C)alkoxy, N-[hydroxy-(2–4C)alkyl]carbamoyl-(1–4C)alkoxy, N,N-di-[hydroxy-(2–4C)alkyl]carbamoyl-(I-4C)alkoxy, (1–4C)alkylamino-(2–4C)alkoxy, di-[(1–4C)alkyl]amino-(2–4C)alkoxy, (2–4C) alkanoylamino, N-[hydroxy-(2–4C)alkyl]amino, N-[hydroxy-(2–4C)alkyl]N-[(1–4C)alkyl]amino, (1–4C)alkylamino-hydroxy-(2–4C)alkoxy, di-[(1–4C)alkyl]amino-hydroxy-(2–4C)alkoxy, N-[amino-(2–4C) alkyl]carbamoyl-(1–4C)alkoxy, N-[N-{(1–4C)alkyl}amino-(2–4C)alkyl]carbamoyl-(1–4C)alkoxy or N-[N,N-di-{(1–4C)alkyl}amino-(2–4C)alkyl] carbamoyl-(1–4C)alkoxy;

n is 1, 2 or 3 and each R² is independently hydroxy, (1–4C)alkylsulphonyl, (2–4C)alkanoylamino, (2–4C)alkanoyl or (1–3C) alkylenedioxy;

or a pharmaceutically-acceptable salt thereof.

16. A pyrimidine derivative of the formula I as claimed in claim 10 wherein m is 1 or 2 and each R¹ is independently hydroxy, methylenedioxy, 2-hydroxyethoxy, 3-hydroxypropoxy, 2-methoxyethoxy, 2-ethoxyethoxy, 3-methoxypropoxy, methoxycarbonylmethoxy, ethoxycarbonylmethoxy, cyanomethoxy, carbamoylmethoxy, N-methylcarbamoylmethoxy, N,N-dimethylcarbamoylmethoxy, 2-(methylamino)ethoxy, 2-(ethylamino)ethoxy, 3-(methylamino)propoxy, 3-(ethylamino)propoxy, 2-(dimethylamino)ethoxy, 2-(diethylamino)ethoxy, 3-(dimethylamino)propoxy, 3-(diethylamino)propoxy, acetamido, N-(2-hydroxyethyl)carbamoylmethoxy, 2-[N-(2-hydroxyethyl)carbamoyl]ethoxy, N,N-di-(2-hydroxyethyl)carbamoylmethoxy, 2-[N,N-di-(2-hydroxyethyl)carbamoyl]ethoxy, N-(2-hydroxyethyl)amino, N-(3-hydroxypropyl)amino, N-(2-hydroxyethyl)-N-methylamino, N-(3-hydroxypropyl)-N-ethylamino, 3-amino-2-hydroxypropoxy, 3-methylamino-2-hydroxypropoxy, 3-dimethylamino-2-hydroxypropoxy, N-(2-aminoethyl)carbamoylmethoxy, 2[N-(2-aminoethyl)carbamoyl]ethoxy, N-(2-methylaminoethyl)carbamoylmethoxy, 2-[N-(2-methylaminoethyl)carbamoyl]ethoxy, N-(2-dimethylaminoethyl)carbamoylmethoxy or 2[N-(2-dimethylaminoethyl)carbamoyl]ethoxy; and n is 1 or 2 and each R² is independently hydrogen, hydroxy, trifluoromethoxy, cyano, methyl, ethyl, methoxy or ethoxy;

or a pharmaceutically-acceptable salt thereof.

17. A pyrimidine derivative of the formula I as claimed in claim 11 wherein m is 1 or 2 and each R¹ is independently hydrogen, hydroxy, amino, fluoro, chloro, bromo, trifluoromethoxy, cyano, methyl, ethyl, methoxy, ethoxy, methylenedioxy, 2-hydroxyethoxy, 3-hydroxypropoxy, 2-methoxyethoxy, 2-ethoxyethoxy, 3-methoxypropoxy, methoxycarbonylmethoxy, ethoxycarbonylmethoxy, cyanomethoxy, carbamoylmethoxy, N-methylcarbamoylmethoxy, N,N-dimethylcarbamoylmethoxy, 2-(methylamino)ethoxy, 2-(ethylamino)ethoxy, 3-(methylamino)propoxy, 3-(ethylamino)propoxy, 2-(dimethylamino)ethoxy, 2-(diethylamino)ethoxy, 3-(dimethylamino)propoxy, 3-(diethylamino)propoxy, acetamido, N-(2-hydroxyethyl)carbamoylmethoxy, 2-[N-(2-hydroxyethyl)carbamoyl]ethoxy, N,N-di-(2-hydroxyethyl) carbamoylmethoxy, 2-[N,N-di-(2-hydroxyethyl)carbamoyl]ethoxy, N-(2-hydroxyethyl) amino, N-(3-hydroxypropyl)amino, N-(2-hydroxyethyl)-N-methylamino, N-(3-hydroxypropyl)-N-ethylamino, 3-amino-2-hydroxypropoxy, 3-methylamino-2-hydroxypropoxy, 3-dimethylamino-2-hydroxypropoxy, N-(2-aminoethyl)carbamoylmethoxy, 2-[N-(2-aminoethyl)carbamoyl] ethoxy, N-(2-methylaminoethyl)carb amoylmethoxy, 2[N-(2-methylaminoethyl)carbamoyl]ethoxy, N-(2-dimethylaminoethyl)carbamoylmethoxy or 2[N-(2-dimethylaminoethyl)carbamoyl]ethoxy; and n is 1 or 2 and each R² is independently hydroxy;

or a pharmaceutically-acceptable salt thereof.

18. A pyrimidine derivative of the formula I

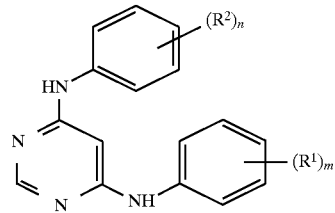

wherein m is 1 or 2 and each R¹ is independently hydroxy, 2-hydroxyethoxy, 3-hydroxypropoxy, 2-methoxyethoxy, methoxycarbonylmethoxy, ethoxycarbonylmethoxy, cyanomethoxy, carbamoylmethoxy, N-methylcarbamoylmethoxy, N,N-dimethylcarbamoylmethoxy, 2-(dimethylamino) ethoxy, 3-(dimethylamnino)propoxy, N-(2-hydroxyethyl)carbamoylmethoxy, N,N-di-(2-hydroxyethyl)carbamoylmethoxy, N-(2-hydroxyethyl)-N-methylamino, 3-methylamino-2-hydroxypropoxy, 3-dimethylamino-2-hydroxypropoxy or N-(2-dimethylaminoethyl)carbamoylmethoxy; and n is 1 or 2 and each R² is independently fluoro, chloro, bromo, trifluoromethyl, methyl or ethyl;

or a pharmaceutically-acceptable acid-addition salt thereof.

19. A pyrimidine derivative of the formula I

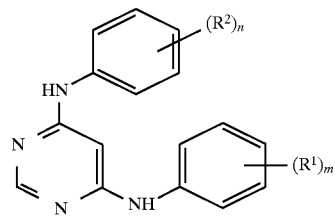

wherein m is 1 and R¹ is independently hydroxy, 2-hydroxyethoxy, 3-hydroxypropoxy, 2-methoxyethoxy, methoxycarbonylmethoxy, ethoxycarbonylmethoxy, cyanomethoxy, carbamoylmethoxy, N-methylcarbamoylmethoxy, N,N-dimethylcarbamoylmethoxy, 2-dimethylaminoethoxy, 3-dimethylaminopropoxy, N-(2-hydroxyethyl)carbamoylmethoxy, N,N-di-(2-hydroxyethyl)carbamoylmethoxy, N-(2-hydroxyethyl)-N-methylamino, 3-methylamino-2-hydroxypropoxy, 3-dimethylamino-2-hydroxypropoxy or N-(2-dimethylaminoethyl)carbamoylmethoxy; and n is 1 or 2 and each R² is independently fluoro, chloro or methyl;

or a pharmaceutically-acceptable acid-addition salt thereof.

20. A pyrimidine derivative, or a pharmaceutically-acceptable acid addition salt thereof, selected from:

4-(3'-chloro-4'-fluoroanilino)-6-[4'-(2-hydroxyethoxy)anilino]pyrimidine,

4-[4'-(carbamoylmethoxy)anilino]6-(3'-chloro-4'-fluoroanilino)pyrimidine, 4-(3'-chloro-4'-fluoroanilino)-6-(4'-N,N-dimethylcarbamoylmethoxy)anilino]pyrimidine, 4-[4'-(2-hydroxyethoxy)anilino]6-(3'-methylanilino)pyrimidine, 4-[4'-(2-dimethylaminoethoxy)anilino]6-(3'-methylanilino)pyrimidine, 4-[4'-(3-dimethylaminopropoxy)anilino]6-(3'-methylanilino)pyrimidine, 4-(3'-chloro-4'-fluoroanilino)-6-[4'-{N-(2-hydroxyethyl)carbamoylmethoxy}anilino]pyrimidine, 4-[4'-{N-(2-dimethylaminoethyl) carbamoylmethoxy}anilino]6-(3'-methylanilino)pyrimidine, or 4-[4'-(3-dimethylamino-2-hydroxypropoxy)anilino]6-(3'-methylanilino)pyrimidine.

21. A pyrimidine derivative of the formula I

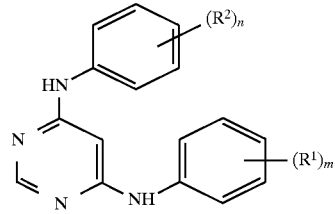

wherein m is 1 or 2 and each R¹ is independently fluoro, chloro, methyl or methoxy; and n is 1 or 2 and each R² is independently fluoro, chloro, bromo, methyl or ethyl;

or a pharmaceutically-acceptable acid-addition salt thereof.

22. A pyrimidine derivative, or a pharmaceutically-acceptable acid addition salt thereof, selected from:

4-(3'-chloro-4'-fluoroanilino)-6-(4'-methoxyanilino)pyrimidine, 4-(3'-chloro-4'-fluoroanilino)-6-(4'-dimethaminoanilino)pyrimidine, 4-(3'-chloro-4'-fluoroanilino)-6-(4'-methylanilino)pyrimidine, or 4,6-di-(3'-methylanilino)pyrimidine.

* * * * *